United States Patent [19]

Holm-Kennedy

[11] Patent Number: 5,466,348
[45] Date of Patent: Nov. 14, 1995

[54] METHODS AND DEVICES FOR ENHANCED BIOCHEMICAL SENSING

[76] Inventor: James W. Holm-Kennedy, 3215 Pacific Heights, Honolulu, Hi. 96813

[21] Appl. No.: 30,791

[22] Filed: Mar. 12, 1993

Related U.S. Application Data

[63] Continuation-in-part of Ser. No. 781,479, Oct. 21, 1991, abandoned, and a continuation of PCT/US92/08940, Oct. 20, 1992.

[51] Int. Cl.⁶ .................................. G01N 27/26
[52] U.S. Cl. .................. 204/153.1; 204/153.12; 204/403; 204/406; 204/414; 204/420
[58] Field of Search ............... 204/403, 153.1, 204/153.12, 406, 420, 414

[56] References Cited

U.S. PATENT DOCUMENTS

| | | | |
|---|---|---|---|
| H675 | 9/1989 | Wortman et al. | 436/152 |
| 4,018,662 | 4/1977 | Ruhenstroth-Bauer et al. | 204/299 R |
| 4,020,830 | 5/1977 | Johnson et al. | 204/403 |
| 4,180,771 | 12/1979 | Guckel | 204/420 |
| 4,181,128 | 1/1980 | Swartz | 604/20 |
| 4,235,864 | 11/1980 | Kaul et al. | 436/542 |
| 4,397,714 | 8/1983 | Janata et al. | 204/153.1 |
| 4,437,969 | 3/1984 | Covington et al. | 204/403 |
| 4,490,216 | 12/1984 | McConnell | 204/153.1 |
| 4,591,550 | 5/1986 | Hafeman et al. | 204/153.1 |
| 4,704,353 | 11/1987 | Humphries | 204/403 |
| 4,727,019 | 2/1988 | Valkirs et al. | 435/6 |
| 4,737,464 | 4/1988 | McConnell et al. | 436/43 |
| 4,741,619 | 5/1988 | Humphries et al. | 356/246 |
| 4,758,786 | 7/1988 | Hafeman | 324/158 D |
| 4,794,089 | 12/1988 | Mroczkowski et al. | 204/403 |
| 4,815,843 | 3/1989 | Tiefenthaler et al. | 356/128 |
| 4,849,330 | 7/1989 | Humphries et al. | 204/153.12 |
| 4,961,833 | 10/1990 | Sakai et al. | 204/403 |

OTHER PUBLICATIONS

"Chemical Sensors–Current State and Future Outlooks" by T. Seiyama, vol. 1, Tokyo, Japan, p. 7, 13 re Decroux Fig. 4 from Bordeaux, Jul. 1–10, 1986, Proc. 2nd Int. Meeting on Chem. Sensors, p. 499.

"Chemical Microsensors" by R. C. Hughes, et al. *Science*, vol. 254 (1991) pp. 74–80 no month available.

*Primary Examiner*—Kathryn Gorgos
*Assistant Examiner*—Bruce F. Bell

[57] ABSTRACT

A method and application for detecting and measuring the presence of a binding target material employs a semiconductor device having a receptor-covered surface topgate, separated by a dielectric layer from a substrate. Receptors attached to this surface exhibit a chemical selectivity function. Binding occurs in a test solution, with charge associated with the target material modulating at least one device characteristic. According to the present invention, measurement may occur under dry conditions, at a time and location different from when binding occurred, thus substantially eliminating problems associated with ionic shielding and reference electrodes, so prevalent with prior art wet measurement techniques. Preferably the device includes a backgate to which a bias may be applied to restore the device's pre-binding characteristics. Measurement of the restorative backgate bias provides a signal indicating binding of the desired target material. The present invention eliminates the reference electrode commonly found in prior art devices and methods. Beads, conjugates and other objects may be used to enhance charge and thus promote sensitivity. Alternatively a distributed channel bipolar device may be used as a sensor. Sensors according to the present invention may be batch produced and combined in arrays with same or differing receptors to provide rapid measurements, including differential and confirmational testing. Such an array may be combined with an electrophoresis gel material to provide enhanced sensitivity, real-time analysis of drifted charged electrophoresis molecules.

50 Claims, 13 Drawing Sheets

5,466,348

METHODS AND DEVICES FOR ENHANCED BIOCHEMICAL SENSING

RELATIONSHIP TO EARLIER FILED APPLICATION

This is a continuation-in-part application of U.S. patent application Ser. No. 07/781,479, filed on Oct. 21, 1991, now abandoned and from P.C.T. application Ser. No. PCT/US 92/08940, filed Oct. 20, 1992, with priority claimed from each.

FIELD OF THE INVENTION

This invention relates to sensing and measuring chemicals in general, and more particularly to methods and apparatus for sensing and measuring chemicals, biochemicals, molecules and sub-molecular components including ions, using semiconductor sensors.

BACKGROUND OF THE INVENTION

Semiconductor sensors for detecting biochemical reactions are known in the art, as exemplified by U.S. Pat. No. 4,180,771 to Guckel (1979). FIG. 1 depicts a typical such prior art sensor 2 used to measure the attachment to a solid substrate surface 4 of a desired chemical compound 6 in a solution 8. Sensor 2 typically is fabricated like a metal oxide silicon ("MOS") field effect transistor, wherein region 10 functions like a channel between source and drain regions 12, 14, and region 16 functions like a gate, but without metalization. Using receptor-type mechanisms 18, region 4 is made sensitive to (and encourages adhesion or attraction with) a desired target substance 6. Alternatively, receptor-like mechanisms 18 may be attached to the device gate 16.

Although region 4 should be relatively insensitive and non-reactive to other chemicals, such as 20, in practice region 4 can respond non-specifically and attach with other than desired target substance 6. For example, solution 8 may also include charged particles 22 of varying size, including positive and negative ions. In biochemical sensing applications, a suitable biochemical environment for the receptor 18 and bio-target 6 dictates that test solution 8 have a relatively large ionic concentration. Unfortunately, relatively large ion concentration for the test solution 8 can adversely affect biochemical measurement due to ionic shielding.

Prior art measurements use a reference electrode to obtain stable and reproducible measurements, which electrode may be attached to sensor 2, e.g., electrode 24, or not attached, e.g., electrode 24' (shown in phantom). The reference electrode is coupled to a reference potential $V_r$, (e.g., ground) and completes an electrical circuit, apparently to provide proper sensor biasing and to eliminate drift. Various bias potentials $V_{sr}$, $V_{gr}$ and $V_{dr}$ are coupled to the sensor, typically referenced to $V_r$. One or more measuring devices, indicated generically by 26, are also coupled to the sensor 2.

If the target substance 6 is present in solution 8, it should attach or bind to receptor 18, bringing electrical charges associated with the target substance. Target 6 attachment also brings mass to receptor 18, and can alter receptor 18's contact potential as well.

Thus, during binding or attachment, these electrical charges associated with receptor 18 influence charge present at region 4 (or gate 16, alternatively) and can measurably alter device 2's substrate bias, which can affect device 2's operating characteristics, including conductance and threshold voltage. By monitoring sensor 2 with detection and measurement equipment 26, these characteristic changes may be detected, indicating a binding of the target substance 6.

Further, charges at region 4 can also manifest a potential that tends to vary somewhat logarithmically with the charge concentration, a phenomenon sometimes used in sensing pH. It is characteristic of the prior art that measurements are made when binding of the target substance occurs, e.g., while sensor 2 is still immersed in solution 8.

Unfortunately such prior art sensors and sensing techniques have several deficiencies, including the use of reference electrodes, the inability to meaningfully directly measure charged particles including biochemicals (especially where the test solution is rich in ions), relative device insensitivity and drift, relatively high sensor production cost, and the perceived necessity to make "wet" measurements, i.e., while the sensor is in solution.

Prior art device reference electrode 24 or 24' unfortunately can contaminate the solution 8, and corrupt measurements. Further, the reference electrode bias $V_r$, can interact unfavorably with any ions 22, 30 present in the solution, e.g., resulting in ionic charge separation and polarization. Because even minute movement or agitation of solution 8 circulates these ions, potential disturbances are created that can affect measurement accuracy and introduce drift.

Further, sensing devices and procedures such as depicted in FIG. 1 do not provide meaningful detection and direct measurement of charged particles, especially such particles exceeding a few angstrom in size, where the test solution has high ion concentration. In some applications, the target to be detected is a charged particle 28 that may be several tens of angstroms or greater in size. It is understood that at other than the iso-electronic pH ("pHiso") level, target substances may exhibit a charge of either polarity, depending upon whether pHiso>pH or pHiso<pH, where pH is the test solution pH.

Unfortunately in FIG. 1, ions 22, 30 in solution 8 can screen out and thus mask or shield the target charged particles. Thus, charges associated with the receptors and/or targets may be neutralized (in whole or part), thus masking the desired attachment signal.

Generally, the effects of an electric field operating over a distance upon charges in a semiconductor (e.g., device 2) are understood and used in field effect devices, such as capacitors, field effect transistors ("FETs"), including metal-insulator-semiconductors field effect transistors ("MISFETs"), metal semiconductor field effect transistors ("MESFETs"), and junction field effect transistors ("JFETs").

To better appreciate the adverse effects of ionic shielding, assume that receptor 18 in FIG. 1 has been charged positively (e.g., as a result of pH buffering of the solution 8), and that target material 6 is not yet introduced into the solution. Since solution 8 may includes ions 28, 30 of either polarity, mobile negative ions (assume 30) are attracted to receptor 18, and mobile positive ions (assume 28) are repelled. The polarized negative ions 30 shield or nullify the receptor 18 charge, causing a net charge of zero to be seen somewhat below the substrate surface 4. At the interface between the receptors 18 and substrate-surface 4 the electric field is substantially zero, and thus the underlying FET is not influenced.

When added to the solution, target material 6 binds selectively to the mating receptor 18. But any material 6 charge experiences shielding due to ions in the solution, and produces an indication of net zero, or reduced charge as indicated by the associated insulator electric field as observed somewhat below the substrate surface 4.

Thus, although a charged target material 6 has bound to the receptor 18, shielding prevents meaningful detection by device 2. Device 2's failure to sense attachment is chronic problem with prior art devices, and may result in a false negative report. But to support certain medical and biochemical reactions of interest (e.g., many anti-body-antigen reactions), the solution must have a relatively high ionic concentration that can result in a shielding length substantially masking, reducing or interfering with detection of the binding-charge induced signal of interest.

This apparent resultant low sensitivity associated with prior art FET type sensors (e.g., sensor 2) has caused such devices to be disfavored as sensors for the direct detection of charged molecules in ionic solutions, especially biochemicals.

The prior art has attempted, largely without success, to improve device sensitivity by attempting to make transient measurements, wherein the attachment signal is measured in the brief interval before nullification results from shielding and equilibrium.

Prior art sensor insensitivity is especially troublesome where relatively small changes ($\Delta S$) in a signal (S) are to be measured. Rather than being able to provide a direct measurement of $\Delta S$, such prior art devices sense $\log(S\Delta S)$ and provide a signal proportional to $\log(S\Delta S)-\log(S)$, at best a relatively insensitive indirect measurement of $\Delta S$. Logarithmic dependent measurements are believed to account for the relatively low sensitivity of typical prior art pH sensors.

Ionic shielding is not the only disadvantage with prior art in-solution sensor measurements. Wet testing can subject the measurements to drift resulting, for example, from ion movement within the solution, and from reference electrode contamination.

Further, in a given application the measurement and detection equipment 26 may require sophisticated and expensive components. Under such circumstance, having to "wet test" requires that the test and detection/measurements occur essentially at the same time and place as the target binding. This restriction can preclude the use of sensors if sophisticated equipment is not readily available in the region where the testing (that possibly leads to binding) occurs.

It would be advantageous if after possible binding, the sensor could be sent, preferably dry, to a remote facility for detection and measurement of any target substance attachment using sophisticated equipment not available at the testing/binding region. Unfortunately, such "dry testing" is not practiced with prior art devices and procedures such as depicted in FIG. 1.

Fabricating many prior art sensor devices is sufficiently expensive as to preclude "use once and discard" practice. Similarly, often the receptor material is scarce or very expensive. Clearly it would be advantageous if devices and/or their receptor materials could be used more than once. In addition, sufficiently inexpensively fabricated devices could be provided in arrays to permit simultaneous testing for multiple target materials, e.g., multiple disease antigens.

Many prior art sensors have limited sensitivity, limited sensor gain, and/or device drift, unfortunate limitations since in many clinical applications, a target biological analyte may exist in a minute concentration, i.e., a few ng/ml for proteins in blood serum. Substantially more sensitive devices would permit the simultaneous use of several different dedicated receptors to provide more rapid (and thus less expensive) testing, including differential analysis testing.

In short, there is a need for an inexpensive field effect type biosensor, preferably a IC-compatible (thus permitting integration with signal enhancing, control and other environmental sensors, all on-chip), that can be inexpensively mass produced using standard semiconductor fabrication technology. Such device should reliably measure biochemical information with high sensitivity, and be substantially free of signal drift.

Further such devices should include multiple receptors, some of which may be dedicated to binding different target materials, and should further include a mechanism for discerning which of several target materials have in fact bound. Further, there is a need for devices that may be fabricated and used in arrays, including arrays containing sensors with multiple types of receptors. Such arrays can promote rapid and relatively inexpensive testing, including differential and confirmational analysis testing. Further, arrays can provide self-testing of the devices themselves, as well as confirming the presence of a suitable environment for valid testing, e.g., acceptable ranges of temperature, and pH.

Preferably such device, and a methodology using such device, should not require a reference electrode, and should be capable of making measurements under wet or dry conditions. Further such device and method should enable detection of a contact potential resulting from the binding of a target material and a receptor, and should include mechanisms to eliminate false positive and false negative measurements.

Further, such device and methodology should provide mechanisms for enhancing the sensitivity of the device per se, for enhancing the effective amount of charge binding to the device, and for amplifying the signal detected by the device. Preferably such mechanisms should be usable and reusable under wet or dry measurement conditions. Preferably measurements could be made not on a transient basis, but by integrating all charge captured by the sensor receptors over preselected time period. Such technique would provide an enhanced signal, enhanced signal-to-noise, and would lend itself to differential analysis.

Finally, such device and methodology should be useful in a wide spectrum of applications including biochemical sensing and measurement, DNA research, pH and hydrogen sensing, pollution sensing, optical and photodetector sensing, pyroelectric sensing, magnetic and force sensing including piezoelectric sensing.

The present invention provides such devices and methodologies.

SUMMARY OF THE INVENTION

In one aspect, the present invention provides a field effect type device that can be used for wet or dry detection and measurement of a binding target material, without requiring a reference electrode. In a first embodiment, the device includes a semiconductor material whose upper surface is covered by an insulator layer supporting a topgate, and a lower surface that supports a bottom gate. When coupled to a power source, the device creates a field effect region, and includes a channel capable of conduction as a function of electrical activity at the top gate and/or bottom gate. The top gate preferably is covered by a binding layer that selectively provides a chemical reaction function in the presence of a predetermined class of target, such as charged particles, bio-particles, chemicals, etc. Other biosensor embodiments provide a distributed channel bipolar device having bipolar and MOS device characteristics, and buried gate devices. However, the present invention is not limited to field effect devices with a conducting channel per se, and alternative structures may also be employed in biosensor applications, e.g., a gated diode, a buried gate capacitor, among others.

Such devices may be implemented in a variety of ways using field effect device phenomena, such as are associated with a junction field effect transistor ("FET"), an exposed insulator FET ("EIFET"), a metal-oxide-silicon field effect transistor ("MOSFET"), a metal-semiconductor field effect transistor ("MESFET"), a metal-insulator field effect transistor ("MISFET"), a heterojunction device, and a field effect capacitor. Further, MOSFET and MISFET type devices may have conductive or non-conductive gates. Further, the device field effect region may be operated in a variety of modes, such as enhancement, depletion, inversion or accumulation. If used, metal or metalized gates should preferably be a chemically inert material if the metal is exposed to solution, or preferably be buried within the device to protect the test solution environment from gate contamination. Metal gates that are allowed to float electrically may be used, or as described herein metal gates may be coupled to a suitable power source using a blocking capacitor to establish a desired direct or alternating current bias condition.

In a first embodiment, the bottom gate may be implemented in several ways, including as a PN junction, a PIN region, and an inversion channel/substrate. Preferably the bottom gate structure is relatively lightly doped such that a voltage applied thereto is dropped primarily away from the channel, to enhance sensitivity of the device. In lieu of having a backgate PN junction, a device according to the present invention may alternatively include a depletion modulatable semiconducting layer, e.g., polysilicon deposited on an insulating or conducting material. In such an embodiment, the polysilicon backgate could form a metal semiconductor junction, a MIS junction, or the like, providing that the backgate structure can bring about depletion modulation of a field effect region in the device.

In use, the device is exposed to a solution containing a target material with which the binding layer will attach. If attachment occurs, the resultant change in attachment charge and/or contact potential will alter the device's quiescent state. Such induced charge effects may be used with a FET-type sensor statically, sequentially, or transiently. Suitable monitoring equipment coupled to the device can detect this change, confirming that the target substance is indeed present, and providing an quantitative measurement. Various amplifying means and feedback features may be used to enhance sensitivity and performance.

In stark contrast to the prior art, in a second aspect the present invention enables device measurement to occur in a dry, or at least quasi-dry state, although measurements may also be made in a wet state. In dry/quasi-dry testing, the device is exposed to a test environment, e.g., a solution, wherein binding with a target substance may occur. The device is then dried such that attached or bound target substance remains attached to the device. The device is then measured dry, quasi-dry, or re-wetted at a later time and different location, if desired.

The present invention's ability to dry measure avoids the ionic shielding problems and resultant low sensitivity associated with prior art wet measurement techniques. As a result, the present invention permits meaningful direct measurements of charged matter, including particles, ions, many biochemicals, nucleic acid chains and components such as DNA and DNA segments, and so forth.

In further contrast to the prior art, the present invention requires no reference electrode, and thus avoids reference electrode contamination of the test solution, signal drift, and ionic disturbances. Mechanisms are disclosed for selectively attaching receptors to desired regions of the sensor, to enhance performance and to protect any other components on the substrate from deleterious attachment effects.

In yet another aspect, the present invention provides various mechanisms, suitable for wet or dry measurements, for enhancing the attachment of target material to the device, for enhancing sensitivity of the device to attached target material, for providing confirmational data including confirmation that the devices themselves are functioning, and for processing signals from the device representing attachment.

Other features and advantages of the invention will appear from the following figures and from the following description, wherein the preferred embodiments are set forth in detail.

DETAILED DESCRIPTION OF THE PREFERRED EMBODIMENTS

Figure 1:
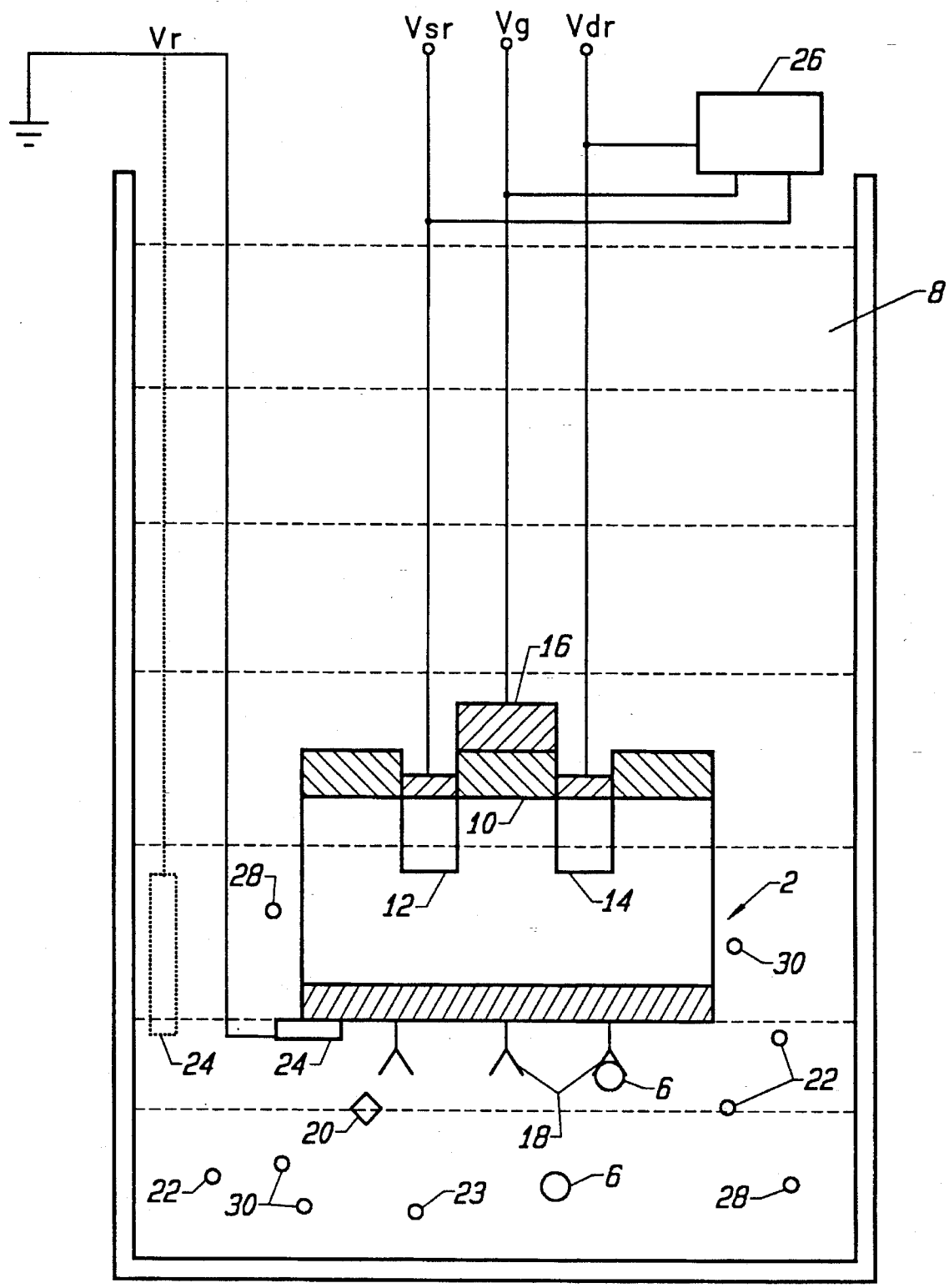
FIG. 1 depicts a generalized sensor and sensor measurement, according to the prior art.
Figure 2A:
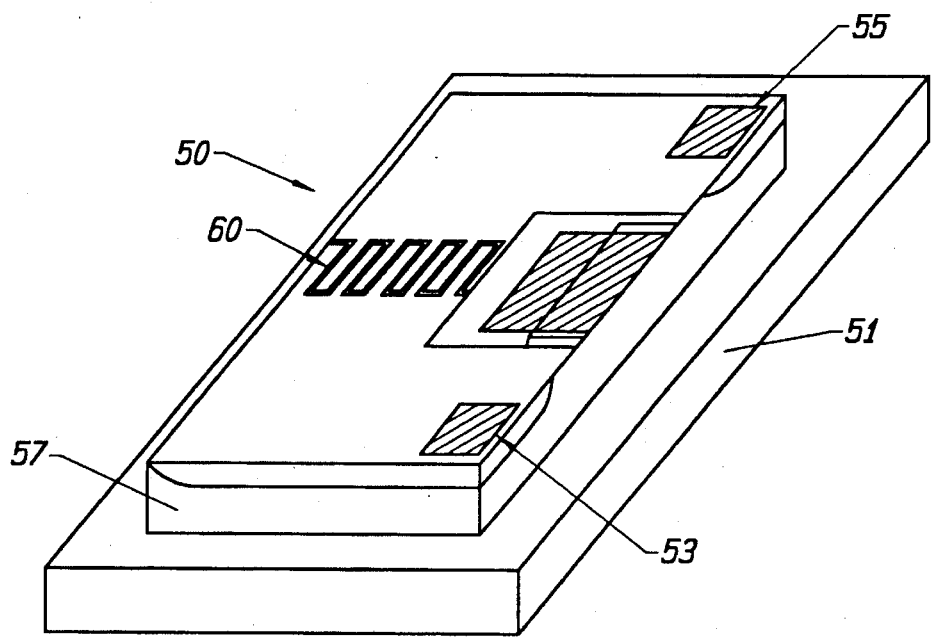
FIG. 2A is a perspective depiction of an EIFET sensor, according to the present invention.
Figure 2B:
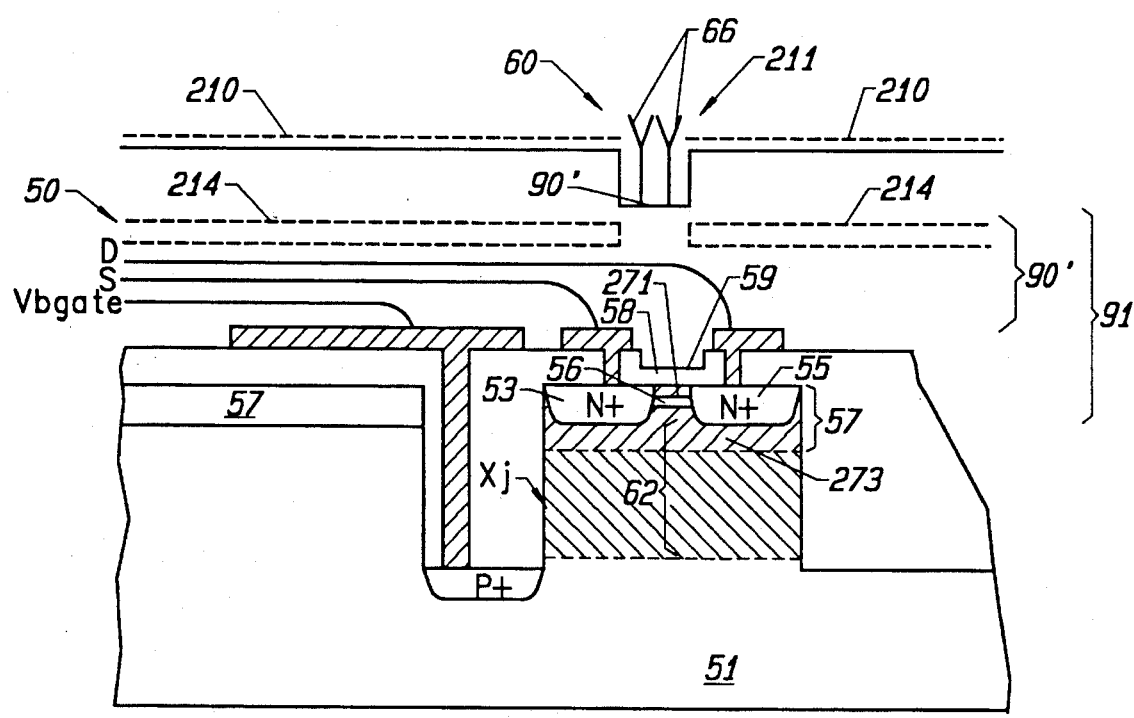
FIG. 2B is a side view of an EIFET sensor, according to the present invention.

FIGS. 2A and 2B depict a sensor 50 implemented as a semiconductor field effect device, such as an FET. Devices according to the present invention, including device 50, may be fabricated in a variety of configurations, including a junction FET ("JFET"), a metal-semiconductor field effect transistor ("MESFET"), a metal-oxide-silicon FET ("MOSFET"), a metal-insulator-silicon FET ("MISFET"), an exposed insulator FET ("EIFET"), an ion sensitive FET ("ISFET"), a distributed channel bipolar device ("DCBD"), a heterojunction device, and a capacitor. Further, semiconductor device 50 may be operated in enhancement mode, depletion mode, or inversion mode. It is significant to note that no reference electrode is depicted or required according to the present invention.

Device 50 includes a semiconductor substrate bulk 51 having a source region 53, a drain region 55, an FET channel 56 capable of electrical conduction, an insulation layer 58 (e.g., $SiO_2$, $Si_3N_4$), an exposed insulator topgate 60, and a bottom or lower gate 62. According to the present invention, channel 56's conductance may be modulated by electrical signals and/or charge present at topgate 60 and/or bottom gate 62. Preferably device 50 is an exposed insulator FET, or "EIFET" with a relatively deep channel 56 (under no backgate bias) to increase device detection sensitivity.

Figure 3A:
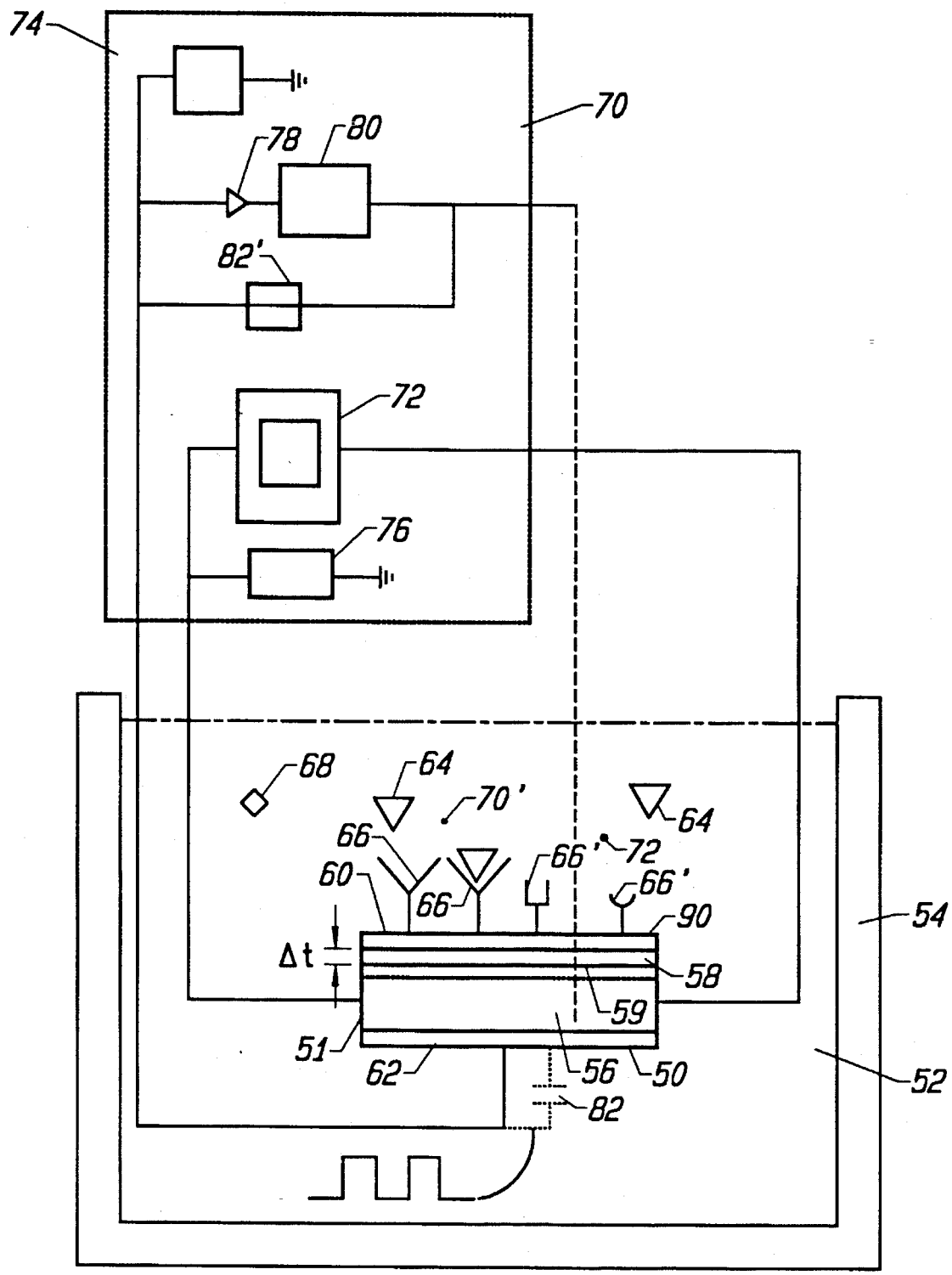
FIG. 3A depicts a sensor and generalized sensor measurement according to a first embodiment of the present invention.

The uppermost surface 59 of insulator layer 58 is preferably covered with a protective moisture blocking film 90. Ideally, film 90 is relatively inert chemically, impervious to any corrosive components in test solution 52, will not contaminate the test solution, and provides an outer surface with many sites for binding with target specific receptor substances 66. Applicant has found parlyene to function especially well as film 90, although other materials could also be used. This structure allows topgate 60 to float at the test solution potential, thus avoiding a topgate bias that could influence the binding reactions at the topgate and introduce erroneous signals. As a result, the surface of film 90 can be made selectively reactive without contamination risk. While FIG. 3A depict target attachment to sensor 50 as occurring in a test solution 52 within a container 54, it is understood that attachment may in fact occur in vitro, e.g., within the human body where solution 52 is a bodily fluid.

Applicant's depletion mode EIFET device (FIGS. 2A and 2B) had a 92.5 nm thickness for layer 58, an approximately 100 nm parylene film layer 90, an n-epitaxial layer channel 56 with 4.6 microns thickness, doped at about $10^{15}$/cc (calculated to be a 3.4μ conducting channel width absent back bias), with W/L≈1432 and source-drain distance L=20 microns. As shown by FIG. 2A, the gate 60 was fabricated with a meanderline pattern to provide a large W/L using the laboratory equipment at hand, to thus enhance device sensitivity. In FIG. 2A, backgate 62 is the pn junction between substrate 51 (p material) and channel 56 (n-epi region 57). Of course other polarity dopants could be used.

Applicant's prototype device was fabricated with relatively unsophisticated equipment. Accordingly, it was not feasible to fully deplete through the device channel due to leakage current generation problems associated with the prototype. However, even with partial depletion of the epi channel, large receptor and target attachment signals were observed. These signals would be even larger for the near total channel depletion condition, enhanced W/L (e.g., 1μ drain-source dimensions) that a commercially fabricated low leaking device should produce. A commercially fabricated device would further permit very high backgate amplification, with further sensitivity enhancement.

According to the present invention, attached charge influences an underlying channel region in a measurable fashion. It is therefore desired that receptors 66 be affixed to the present invention 50 over the topgate region 60, but not elsewhere. Generally in an integrated circuit, the overlying field insulator layer does not protect underlying regions against attached surface charge, which act through a distance independently of insulator thickness. (By contrast, electric fields from IC voltage traces generate electric fields that are inversely dependent upon the field insulator thickness.) With reference to FIG. 2B, selective receptor attachment can occur in several ways.

With reference to FIG. 2B, in one embodiment the uppermost surface of device 50 is masked with an inert agent or blocking agent 210 that blocks attachment to material 66 such that only the region 212 over the topgate 60 remains unmasked and thus receptive. The device is then exposed to a solution containing the desired receptor material 66, which attaches over the topgate region 212, but not elsewhere due to the blocking material mask 210.

Alternatively, mask 210 may be a preselected blocking chemical with a predetermined charge polarity, chosen such that underlying regions (e.g., devices or circuits) are not unduly influenced by charge attached to mask surface 210. Where a specific masking chemical layer 210 has been patterned to protect underlying regions, post target attachment treatment can be used, such as preparation with a buffered pH solution corresponding to the layer 210's isoelectronic point. Layer 210 is preferably formed using photo patterning techniques.

In another embodiment, the device includes metalization patterns 214 that preferably shield all of the device save for the desired topgate region 212. Preferably the metal mask 214 is covered by a layer of a material 90, e.g. parylene, to minimize possible test solution contamination by the mask. The device is then exposed to a solution containing the desired receptor material 66. Receptors 66 attaching over the topgate region 212 will be in field communication with the underlying channel region 56, whereas receptors attaching elsewhere will have their charge (and indeed any subsequently attached target material charge) shielded from influencing regions outside of the topgate region 212 by the metal mask 214, which is coupled to a DC potential or ground.

Figure 5:
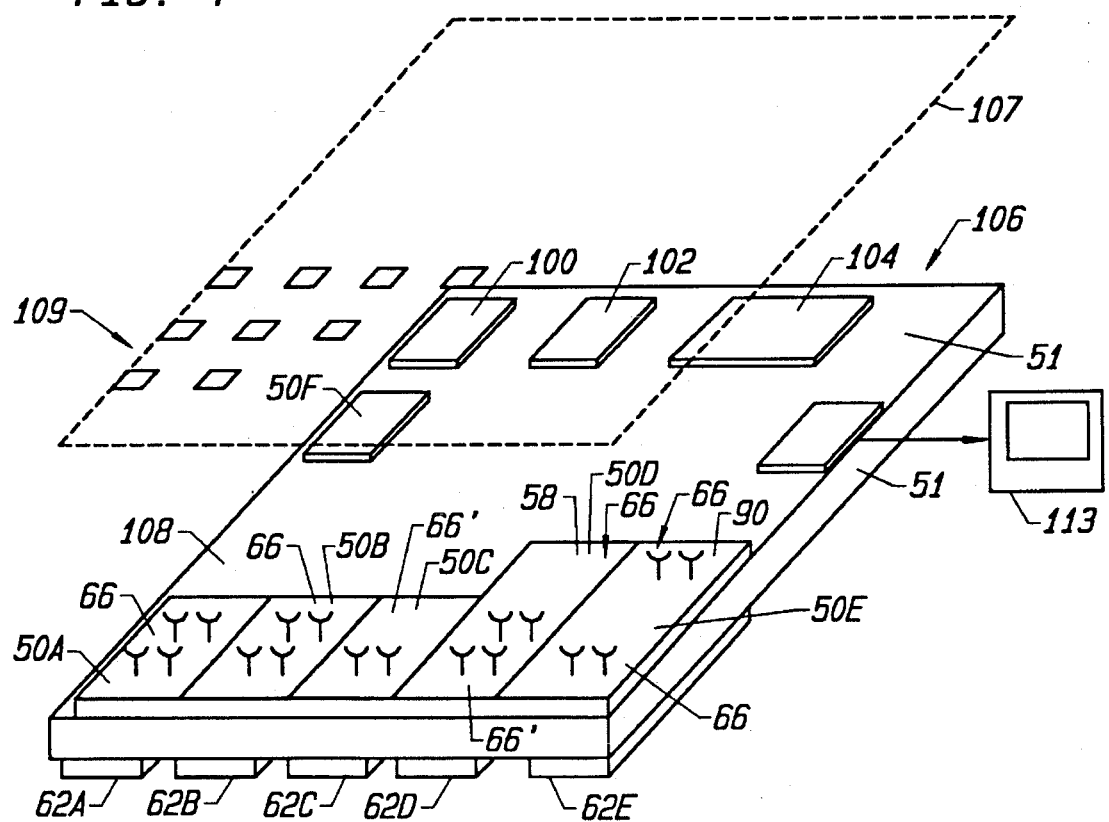
FIG. 5 depicts an embodiment for a sensor array that includes sensors having multiple receptors including neutral receptors, and sensors with on-chip memory, and depicts the use of such an array in an electrophoresis application.

The buried metal potential is selected so underlying regions are not unduly influenced by charge carrying chemicals attached above the shield region 214. Thus, shielding, including buried metal masking, is especially desired where the substrate 51 includes other components, such as depicted in FIG. 5. The metal (or heavily doped polysilicon) charge shield 214 prevents accidental shorting between devices (such as those depicted in FIG. 5) and electronic circuitry incorporated on chip. Wherever a device requires top gate exposure to fluid or analyte, the shield is patterned to provide the requisite opening. But for the desired shielding action provided by the mask 214, performance of some of the other components (e.g., 100, 102, 104), such as the temperature sensor disposed beneath receptor material 66 could undesirably be influenced by the resultant electric field changes produced by the receptors and/or any targets attached thereto.

A selected primary receptor 66 is selectively attached to the outer surface of film 90, during or after fabrication of device 50. Essentially primary receptor 66 dedicates device 50 to bindingly detecting a mating target substance 64, but not other substances 68, 72 that may be present in the solution (see FIGS. 3A, 3B), which other substances may include charged materials and positive and negative ions. As depicted in FIGS. 5A and 5B, device 50 may in fact include two or more receptor types 66, 66', each of which is dedicated to bind with a different target material.

Alternatively, where simultaneous testing for multiple target materials is desired, an array of sensors incorporating one or more specific receptors, may be used (see FIG. 5). Such sensor arrays may be prepared for sensing multiple target substances using photo-patterning known to those skilled in the relevant art. An additional advantage of an embodiment such as FIG. 5 is that degradation of device sensitivity due to long lead and contact resistance can be reduced by integrating associated circuitry (100, 102, 104) on a common substrate with on-chip interconnects. Such on-chip interconnects further minimize test solution contamination associated with lead contacts and electrodes.

While generally the particle or target substance 64 will be a chemical or biochemical, the present invention can also test for the presence of photons, the effects of force, magnetic fields, electric fields, and the like. As used herein, "chemicals" includes not only solutions, molecules, ions, and atoms, but also subatomic particles, such as electrons. As used herein, "biochemicals" includes not only biochemical compounds such as sugars, fats, proteins, etc., but also polymers such as proteins, nucleic acids, glycosaminoglycans, and the like, and encompasses microorganisms and fragments thereof, such as bacteria, viruses, and protozoa.

With reference to FIG. 2B, preferably, applicant's depletion mode EIFET structure includes a lightly doped n-epi layer 57 (e.g., the built-in channel) fabricated on a low resistivity p substrate 51 (with the p-substrate doped preferably much lighter than n channel doping for sensitivity enhancement purposes), wherein N+ regions 53, 55 form the device source and drain regions. The gate 60 structure is somewhat similar to a JFET with a MOS gate (but without metalization), instead of a top PN junction. Like a JFET, the device has a built-in channel 56 that is normally on, with the depth of the built-in channel (and thus channel conductance) controllable via a reverse bias coupled between source 53 and substrate 51.

While the present device 50 provides good sensitivity, sensitivity enhancement mechanisms and structures can provide yet additional sensitivity. Typically the topgate bias causes depletion or accumulation of the channel region 56 immediately under the topgate 60. (Alternatively, if the device 50 incorporates an inversion channel, topgate bias influences the extent of the inversion, e.g., channel conductance.) The backgate is preferably reverse biased to permit the device to operate in a highly sensitive regime under pre-attachment conditions. A relatively small change in a gate attached charge modulates channel top depletion width 271 (see FIG. 7B) and channel conductance. This condition also requires the largest restoration backgate potential 74, 234 (FIGS. 3A, 6A) to reset the device 50 to the pre-attachment condition.

Figure 6A:
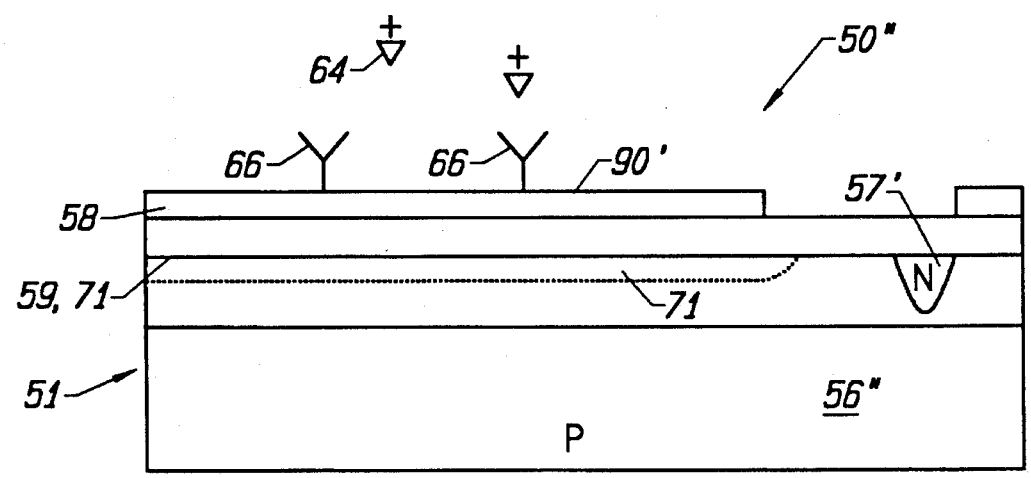
FIG. 6A depicts a gated bipolar sensor embodiment having no channel, according to the present invention.
Figure 6B:
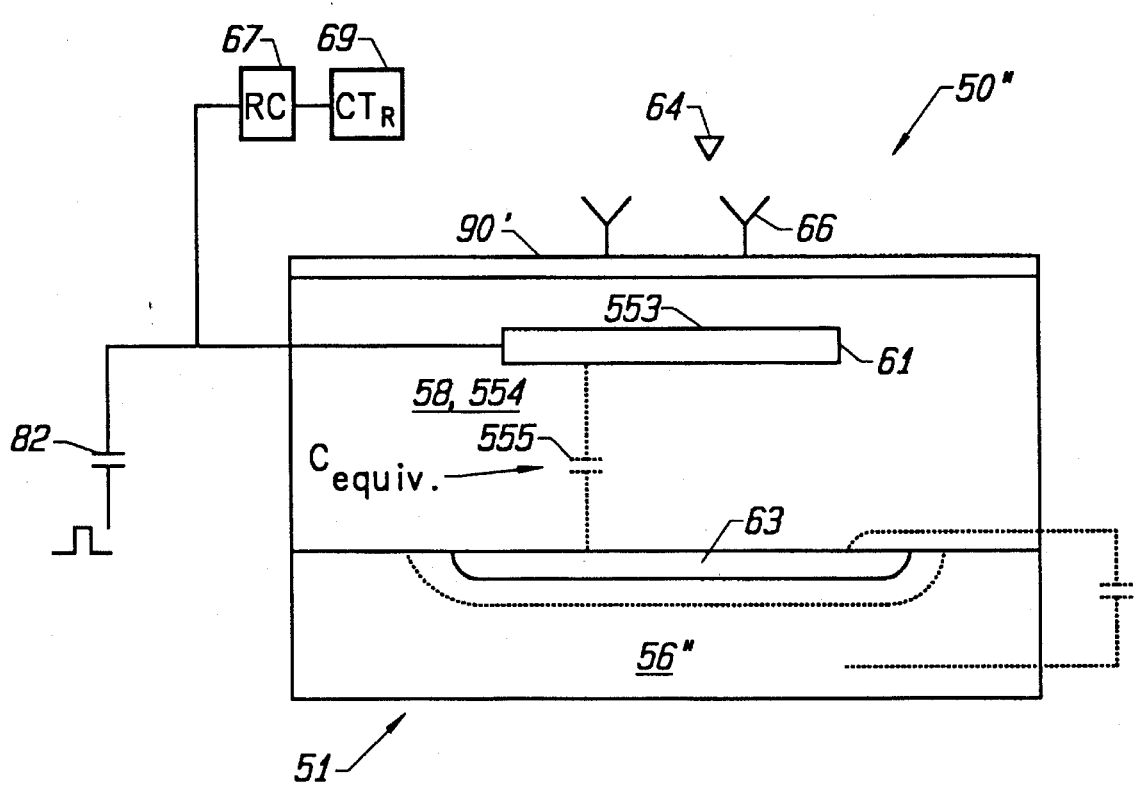
FIG. 6B depicts a buried gate sensor embodiment, according to the present invention.
Figure 6C:
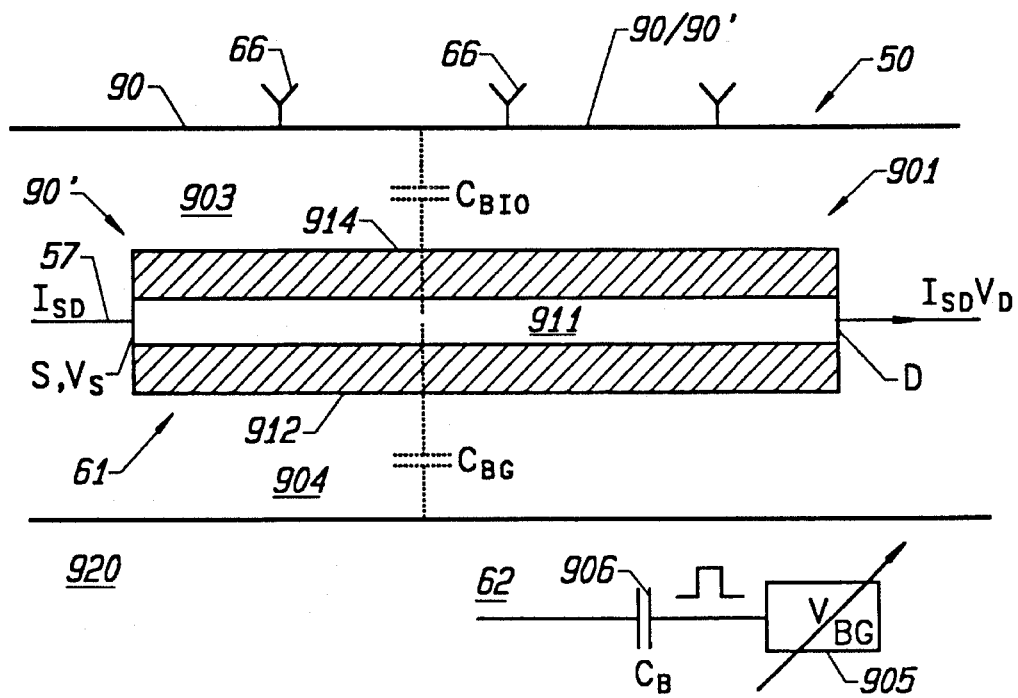
FIG. 6C depicts a sensor with a buried polysilicon conducting channel, according to the present invention.
Figure 6D:
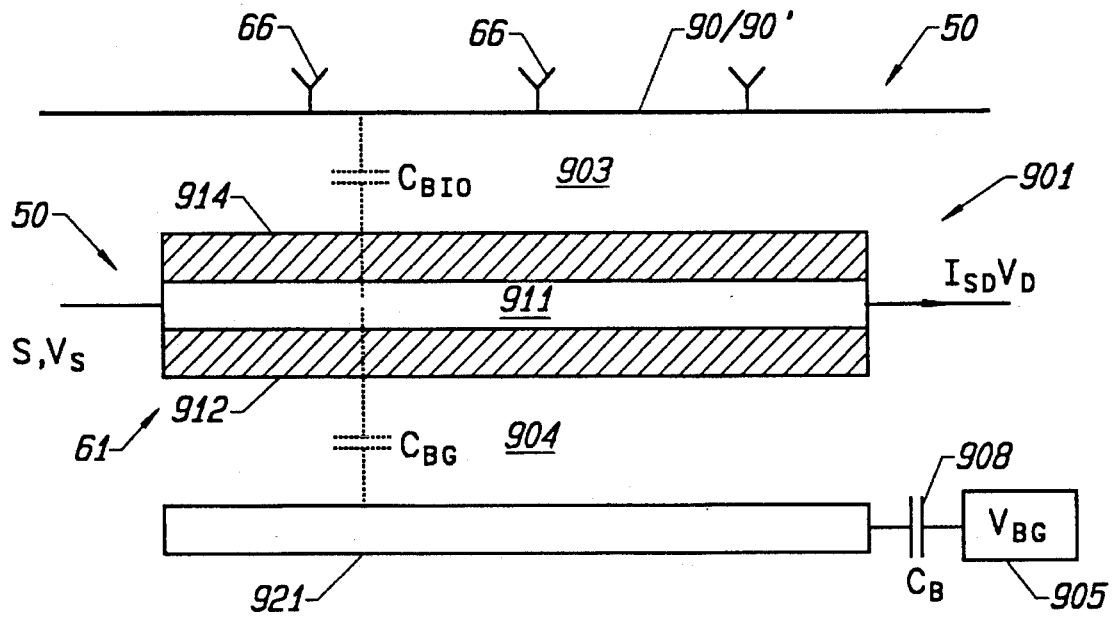
FIG. 6D depicts a sensor with a buried polysilicon channel and buried gate, according to the present invention.
Figure 6E:
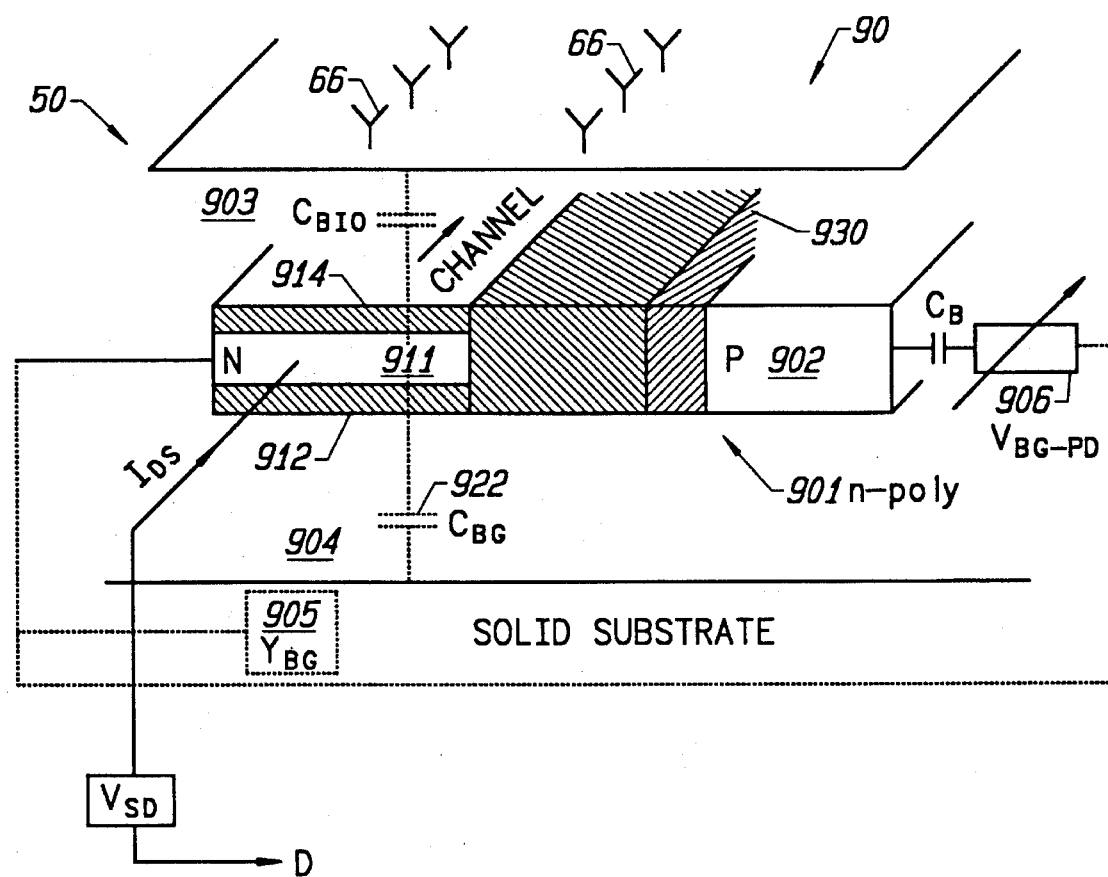
FIG. 6E depicts a second embodiment of a buried channel device, according to the present invention.
Figure 6F:
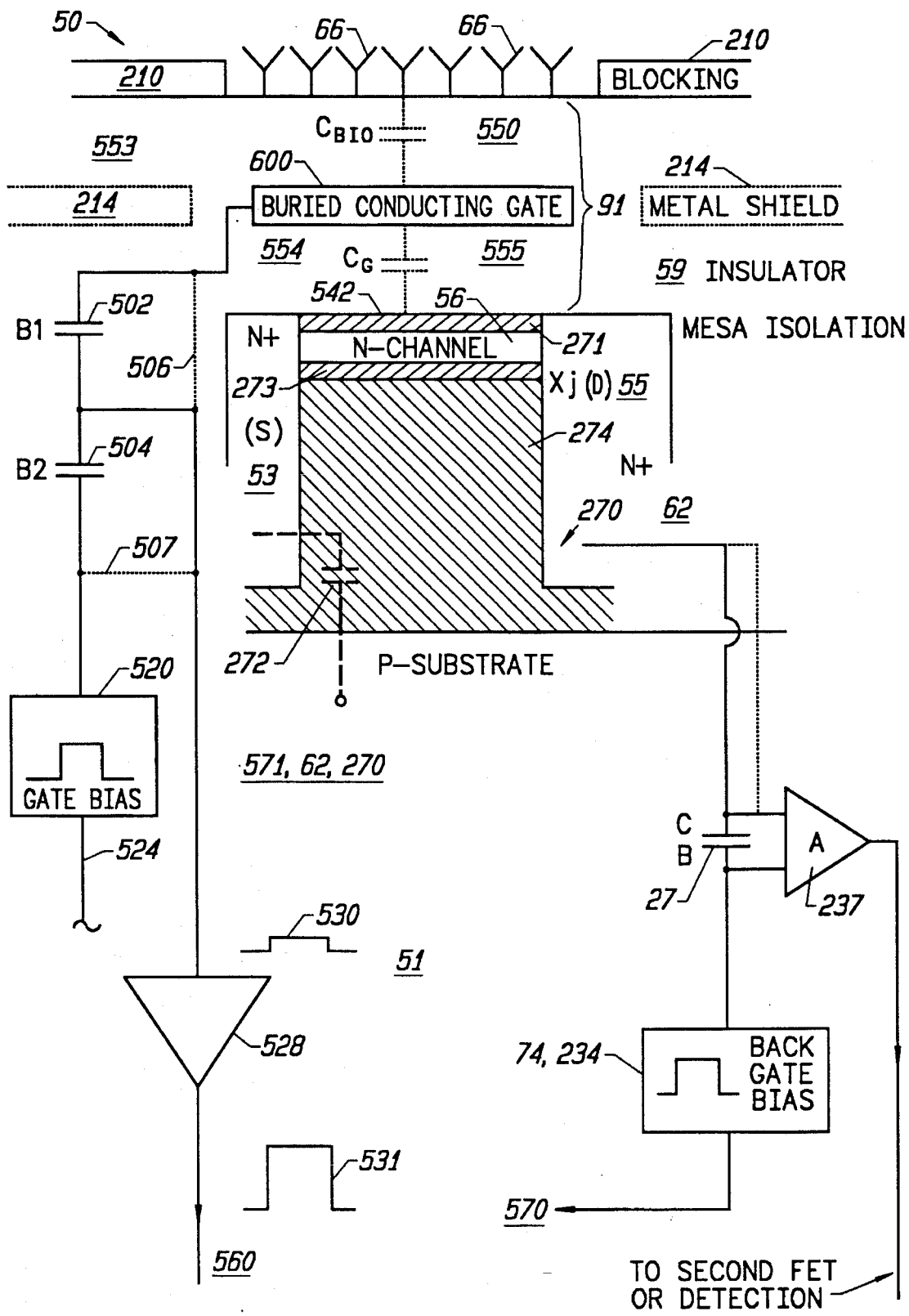
FIG. 6F depicts a capacitively biased buried gate embodiment of a sensor device, according to the present invention.

With reference to FIGS. 3A and 6F, preferably a device according to the present invention uses backgate bias 74, 234 to restore device operating characteristics to a preattachment condition, where a device operating parameter is selected as a reference value. For example, the reference parameter can be source-drain current, pinch-off voltage, transconductance characterized by AC signals, source-drain voltage for constant source-drain current, etc.

In this operation mode, the device backgate 62, 270 is biased to restore the preattachment reference parameter. For example, if attachment increases channel depletion 271 in the depletion mode, a preattachment reverse backgate bias would require magnitude reduction to restore preattachment operating drain current, where source-drain voltage was held constant. The shift in backgate bias to restore the preattachment condition provides a measure of attachment. In operation, the backgate voltage preferably almost pinches off the channel 56 before attachment of charge to the topgate. This bias regime permits the largest percentage change of channel resistance and current to be determined, and advantageously requires the largest restoring back bias voltage.

The use of a measurable backgate bias to a restore preattachment condition permits automation using circuits and components known to those skilled in the relevant art. With reference to FIG. 6F, for example, a capacitive or resistive voltage divider providing a controllable output voltage coupled to the backgate could be used with a simple feedback circuit 240 to reestablish drain-source current, the amount of restoration voltage providing a measure of the attachment condition.

Figure 7A:
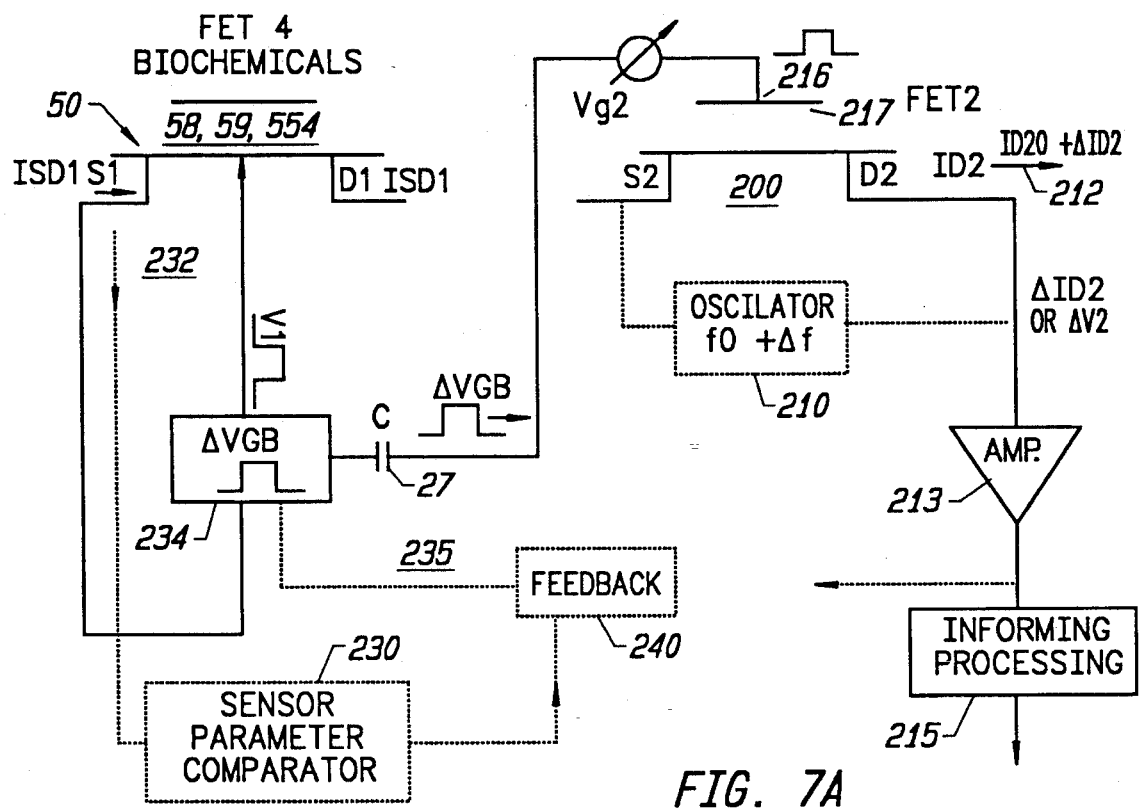
FIG. 7A depicts a cascode arrangement for signal enhancement, according to the present invention.

As shown in FIG. 7A, a reference pulsed drain-source current 212 could also be maintained with a pulsed backgate voltage 234. The resultant pulsed current could be detected and used to adjust, via feedback, the pulsed backgate voltage to restore the current to the pre-attachment value. Alternatively, a pulsed AC drain-source current dependent upon device transconductance could be used. The use of AC signals such as time dependent backgate pulse voltages advantageously permits DC blocking capacitors 27 to be used, AC amplification 213 to be incorporated free from DC drift influences, and allowing AC filters to reject noise to enhance device sensitivity.

According to the present invention, sensitivity enhancement occurs because for PN junctions (i.e., a backgate pn junction 270, or a reverse biased channel-substrate 270), the amount of depletion resulting from a small reverse bias voltage change is generally dependent upon the initial reverse voltage magnitude. For example, for a one-sided abrupt junction whose n-side is doped at $10^{15}/cm^3$, the depletion width is approximately 5 μm at 20 V reverse bias, and is about 6 μm at 40 V reverse bias. It is this nonlinearity that may be used to increase measurement sensitivity in a device employing a suitable backgate.

Thus, substantially reverse biasing the backgate requires a relatively large incremental change in reverse bias (compared to an initial lower-reverse bias potential) to provide a desired small incremental change in backgate depletion width necessary to reset or reestablish preattachment channel conductance. Where source-drain output current is to be maintained, the backgate potential is modulated to restore the conducting channel to a preattachment conductance. Whether an increase or decrease in backgate reverse bias 74, 234 is required will depend on whether attachment increases or decreases depletion or accumulation beneath the gate region 60. The magnitude of voltage change 74, 234 to restore preattachment channel condition increases with increasing initial backgate bias, thus enhancing device detection sensitivity to attachment.

With reference to FIG. 7A, if this incremental backgate bias change 74, 234 is then coupled to the gate 216 of another FET device 217, (FET 2), a much larger output signal 212 is available from FET 2 than would have initially been present in the first device 50 due to attachment induced conductance modulation effects. In this fashion, device attachment sensitivity is increased. If the backgate 62, 270 is operated in AC pulsed mode, AC amplification of the signal delivered to the second device can yet further enhance sensitivity.

Device 50 can be designed to enhance sensitivity by selection of dopant and doping profiles for the pn junction comprising the backgate region 62,270. Where both regions are homogeneously doped, depletion extent will be the same on either side of the junction. If however one region 273 is more heavily doped than side 274, then 273's side exhibits a shallower depletion extent, as depletion is inversely proportional to the homogeneous doping ratio. For example, if the junction's n side is $10^{+4}$ more heavily doped than the p side, applying a given incremental reverse backgate bias results in about $10^{-4}$ of the incremental bias falling across, and modulating, the n region. Stated differently, a substantially larger incremental voltage must be applied to the backgate 62, 270 to restore a preattachment state than would be the case if the two sides of the junction were equally doped. In essence, the two sides of the pn junction perform a voltage division function, providing a desired small fraction of the total backgate bias change to modulate the channel side of the backgate junction depletion, and thereby modulate the channel conductance. Non-linear junction doping can also enhance this desirable sensitivity enhancement feature of a backgate, according to the present invention.

Other back gate junctions may be used with the present invention to enhance target detection sensitivity. A P-I-N backgate substantially enhances sensitivity using a large intrinsic region, dropping a large fraction of applied backgate restoring potential across the I region. In this example, a very small fraction of the backgate bias modulates the n-channel width, leading to especially large sensitivity enhancement.

FIG. 3A depicts a first preferred "wet" measurement embodiment wherein a device 50 contacts a test solution 52 within a container 54, such as a microtiter plate. In operation, film 90 and receptor 66 portion of device 50 are exposed to the test solution 52, allowing any target substance 64 present to bind or attach. Because substance 64 has an associated electrical charge, post-attachment electrical charges will be present at receptors 66, which post-attachment charges can affect device 50 performance.

As noted, for certain embodiments semiconductor device 50 will generally include at least one field effect region wherein the conductance of a channel 56 is modulated is response to electrical or charge activity on one or more gates 60, 62. Such charge (from bound target 64, for example) creates an electric field that operates through the thickness Δt of a typical dielectric insulating layer 58 (e.g., $SiO_2$) and terminates on charges within the semiconductor, thereby altering the semiconductor channel region 56. The magnitude and quantity of such bound charges alters the resistance of the conducting channel. For various embodiments, a buried gate structure may advantageously be used, as described elsewhere herein.

For a FET device, the electric field modulation of the channel conductance (or resistance) alters the typically drain-source current flow in the channel. Charge binding thus alters one or more otherwise quiescent characteristics of device 50, which alteration may be sensed and measured, qualitatively and/or quantitatively, using equipment 70. The measurable characteristics may include, without limitation, drain current, change in threshold voltage, pinchoff voltage, gate-source voltage, transconductance, conductance, gate-source capacitance, gate to substrate capacitance, back gate capacitance, transconductance threshold voltage, "DCBD" and gated bipolar devices bipolar current gain "DCBD" transconductance (DCBD), and change in source voltage for constant drain current.

For example, the attachment of a target-originating charge sheet results in an associated electric field generated across a thickness of insulator material, which results in a threshold voltage shift in an insulated gate field effect device. The resultant incremental threshold voltage change alters the device's operating characteristics, which characteristics may be used to influence an associated circuit to provide an enhanced measurement signal representing attached charge. For example, such measurement signal may reflect switching time, oscillator frequency (where the device is incorporated in an oscillator circuit), channel transconductance, output current into a bipolar transistor base, etc. Further details regarding field effect theory and modelling may be found in a number of standard treatises, including "Device Electronics for Integrated Circuits", 2nd ed., by Muller and Kamins, published by John Wiley.

In the configuration of FIG. 3A, attachment measurements are made while device 50 is still in the solution 52, typically at the time of attachment, or in some other solution (here shown as 52 also) whose pH, temperature, chemical composition, etc. may differ from test solution 52. As shown, during measurement device 50 is coupled to measurement equipment 70, which preferably includes one or more measuring instruments 72 such as an oscilloscope, current probe, semiconductor parameter analyzer or curve tracer, capacitance measuring instrument, specially designed instruments sensitive to the sensor parameters of interest, and the like. Equipment 70 also includes a variable power source 74 that is preferably coupled to device 50's bottom gate 62. Optionally, equipment 70 can include an additional power source 76, coupled to device 50, for establishing a pre-binding quiescent state.

When a target substance 64 binds to a receptor 66, the associated substance charge and/or contact potential will alter device 50's conductance state. For example, depending upon the mode of device 50, a binding condition can be associated with an increase or decrease in channel conductance, a change in drain current or pinch-off voltage or threshold voltage, a change in transconductance, in channel width or depletion, and so on. One or more such characteristic changes may be measured by equipment 70 to provide a signal corresponding to attachment.

Preferably the variable power source 74 is adjusted, post-attachment, to restore whatever pre-attachment quiescent condition existed for device 50. Equipment 70 can measure the amount of restoration bias required from power source 74 to provide an increased measure of the attachment. The compensating or restoration bias can be amplified, e.g., by amplifier 78, and the amplified signal coupled to one or more additional components 80. Component 80, in turn, could include a second device 200, coupled to perform a cascode amplification function upon the amplified restoration bias signal. Second device 200 might be a unijunction transistor, for example, that is triggered into conduction by target attachment to first device 50. If desired, the compensation bias signal from potential source 74 may be coupled to a feedback circuit 82' to automatically provide and maintain proper restoration bias (see also FIGS. 6A and 6B). The design of such feedback circuitry is well known to those skilled in the relevant art, and thus detailed information is not here presented.

With further reference to FIG. 3A, as indicated by capacitor 82, the restorative bias from potential source 74 could in fact be an AC coupled pulse train, wherein one level corresponds to "pre-binding" and a second level of the pulse train corresponds to "post-binding". Because such pulse train signal is AC, capacitor 82 can decouple undesired effects of power source. This facilitates AC amplification of the detected signal, reducing susceptibility to problems associated with drift in DC amplifiers, power sources, etc. Further, capacitor 82, coupled in series with the bottom gate 62 as shown, determines the extent an applied AC compensating reverse bias from power source 74 affects device 50's channel conductance, or other operating characteristics. Voltage division, e.g., with a resistor or a capacitor voltage divider, can also provide a "sensed" voltage gain, wherein a small fraction of the power source is used as a restorative potential, with the total power supply potential being measured to indicate the amount of gate charge attachment to be sensed.

Figure 3B:
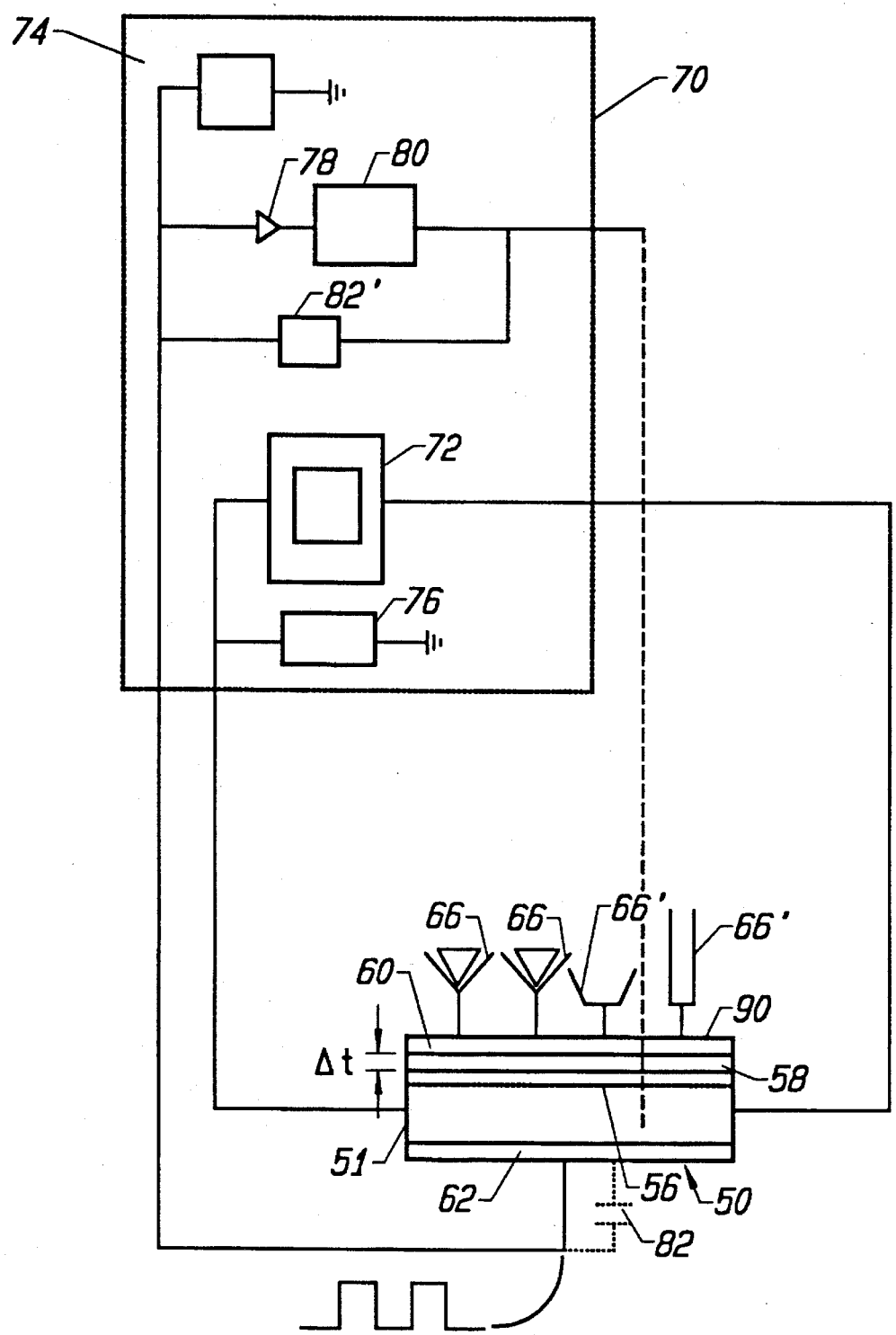
FIG. 3B depicts a sensor and generalized sensor measurement according to a second embodiment of the present invention.

The embodiment of FIG. 3B is similar to what has been described except that while binding occurs in solution (as in FIG. 3A), dry measurements are made. In practice, device 50 is exposed to the test solution 52 potentially containing the target substance 64. It is understood that in this embodiment, equipment 70 need not be present when or where device 50 is tested. Device 50 is then removed from the test solution 52, dried (e.g., by flowing with an inert gas such as nitrogen), and eventually coupled to equipment 70 for measurement. Measurement may occur relatively long after device 50 was exposed to the test solution 52 (e.g., hours, days, weeks) and measurement may occur at a site remote from where attachment potentially occurred. Lyophilizating the sensor soon after binding attachment may further promote longevity of the stored charge mechanism, although this was not tried by applicant. The present method advantageously permits enhancement of measurement accuracy and sensitivity, and confirmational analysis, wherever the measurement is eventually made. Materials needed for measurement enhancement and any confirmational testing need not exist only at the measurement site, and not at the testing site.

Figure 4:
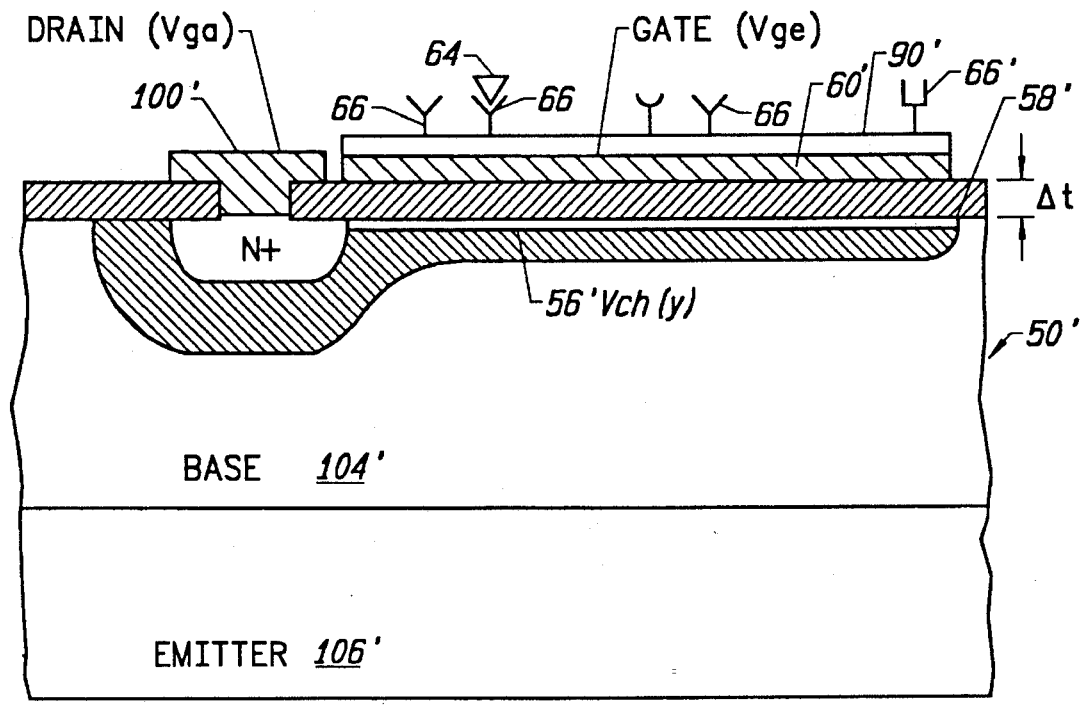
FIG. 4 depicts an alternative embodiment for a sensor, using a distributed channel bipolar device.

While FIGS. 3A and 3B depict one sensor embodiment 50, it is understood that wet or dry measurements, including backgate compensation may be utilized with other biosensors described herein. For example, FIG. 4 depicts another preferred sensor embodiment that is very well suited for detecting binding attachment in a sensor application. Device 50' is a so-called distributed channel bipolar device ("DCBD"), similar to what is disclosed in U.S. Pat. No. 4,885,623 to James Holm-Kennedy, et. al. (1989). The DCBD structure of device 50' includes FET components gate oxide insulation layer 58', an appropriate moisture blocking layer 90', gate 60', drain 100', channel region 56', as well as bipolar components base 104' and emitter 106'. While FIG. 4 depicts a DCBD device with vertical architecture, alternatively, a DCBD device could be fabricated with lateral architecture, or a combination of vertical and lateral architecture. Similar to what was set forth above with reference to device 60 of FIGS. 3A and 3B, in sensor applications, the gate 60' supports an moisture blocking protective film 90' to whose outer surface primary receptors 66' are attached.

As described in detail in said U.S. Pat. No. 4,885,623, depending upon mode of operation, the DCBD may be treated as an FET device with a bipolar source or drain that may be distributed. The DCBD may also be treated as a bipolar device with an FET emitter or collector that may be distributed, or as a gated bipolar device. The DCBD may be operated in enhanced or depletion mode. Further, vertical and lateral bipolar devices can be incorporated in a DCBD device. The FET portion of a DCBD device may incorporate a MESFET, JFET, or IGFET structure.

DCBD devices are especially well suited for sensor wet and dry testing, according to the present invention. DCBD devices exhibit high transconductance and current gain sensitivity to relatively small changes in gate voltage or gate charge, resulting from the binding of a target substance to the device. DCBD devices are also very sensitive to small changes in base current, under certain operating conditions. Further, as described elsewhere herein, techniques may be employed to enhance various DCBD parameters in response to target binding. Such enhanceable parameters include bipolar gain, gate and base current dependent current gain, heterogeneous channel behavior, effective gate area and gate shape, and transconductance threshold voltage effect. Transconductance measurements with device 50' are especially advantageous because a null may be detected using alternating current ("AC") amplifiers, operating at high gain. According to the present invention, a DCBD device may have a conducting gate 60' that floats, or is capacitively charged (as described herein). Alternatively, a conducting channel 56' may be used, without a conducting gate, the channel being, for example, an inversion channel or a buried channel.

Independent of the sensor type used, at the measurement site, a substantially equivalent buffered rinse solution is prepared, preferably with a pH equal to the test solution pH, to minimize changes of attached charge, in either magnitude or sign. Where the device includes an onboard mechanism for storing the test pH value, the test pH may be read from the device itself, otherwise the test pH is preferably known. Preferably morpholinopropanesulfonic acid ("MOPS") is used as a buffered solution for the rinse-measurement operation, as was the case for the test example described in FIG. 9 (IgG system). Other buffers may be preferred depending upon the test, system under investigation. If the rinse and test solutions are different, empirical measurements of the relative influences of the different solutions may be determined and used, and appropriate rinse lengths, charge influences, temperature, etc., incorporated for adjusting the measurement results appropriately. However, essentially identical pH values will replicate the initial binding reaction environment. One or more receptor chemicals, additional to the primary receptor 66, attached to a second sensor on a test chip, may be used to characterize different influences of different buffers, pH, etc., and to correct test sensor data.

Figure 9A:
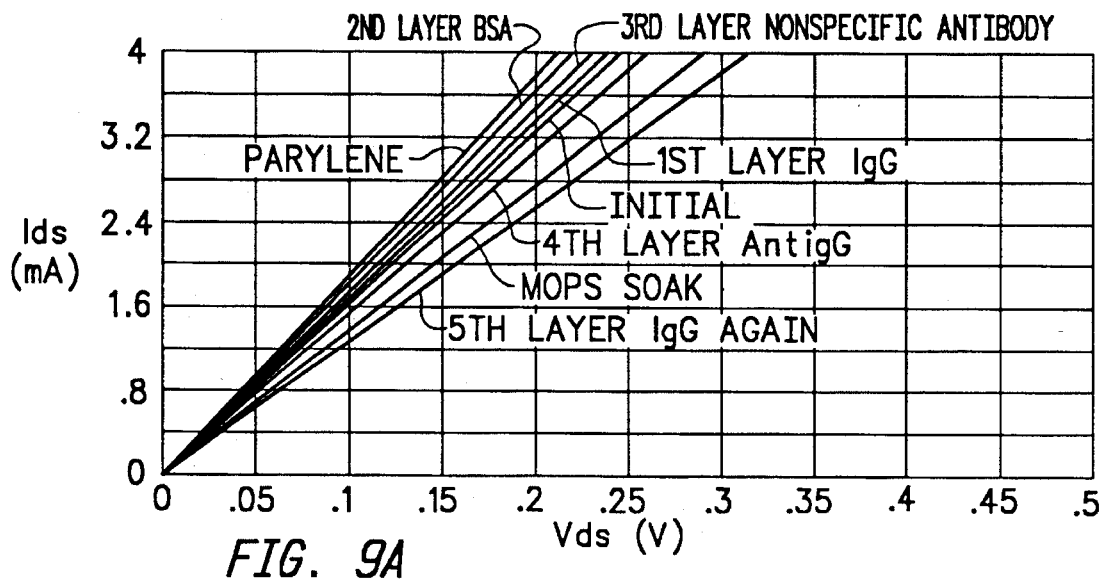
FIG. 9A depicts changes in the characteristics of a device according to the present invention, in response to different attachment phenomena.
Figure 9B:
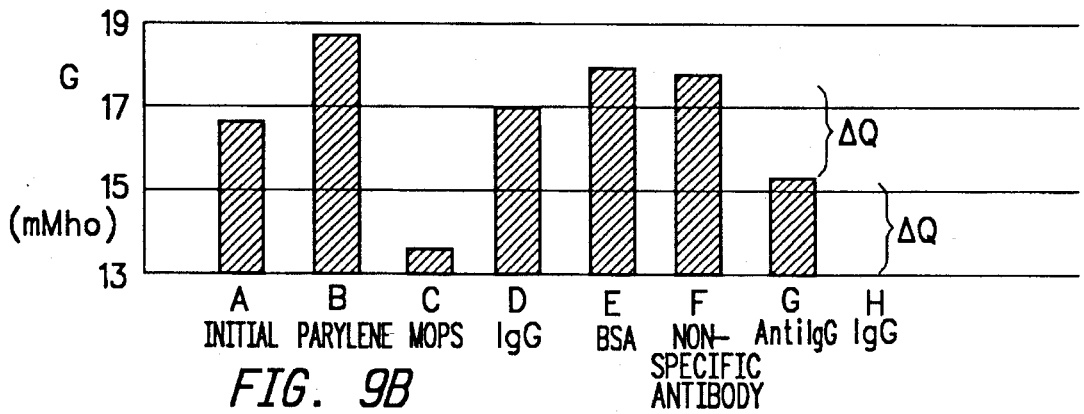
FIG. 9B is a bar graph conductance depiction of the slope of the data shown in FIG. 9A.
Figure 9C:
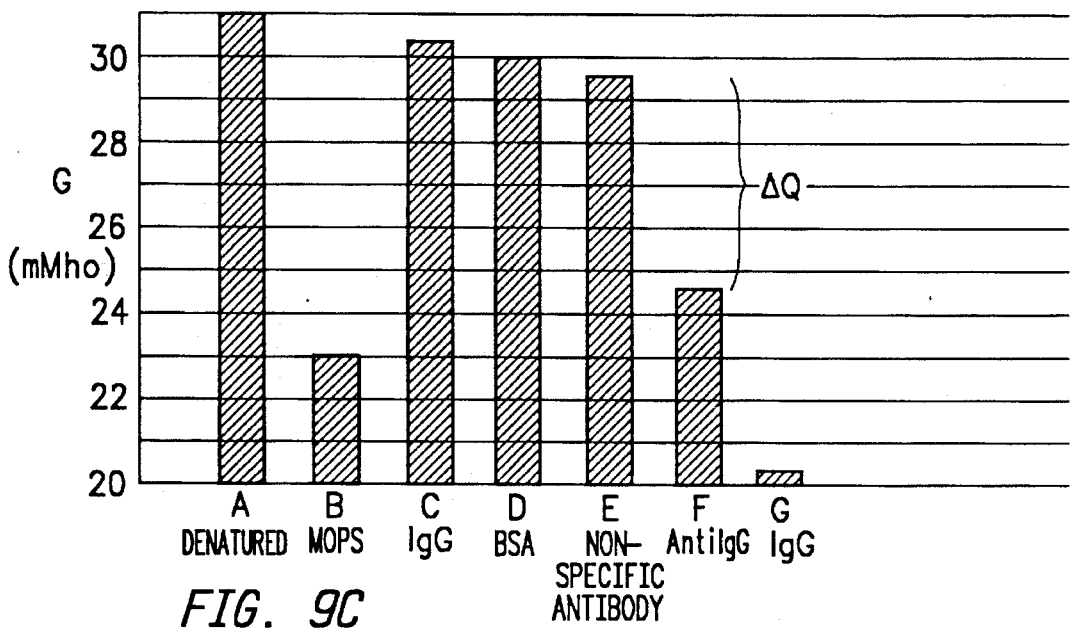
FIG. 9C is a bar graph depiction of conductance change in a device according to the present invention, in response to exposing the device to various solutions including a denaturing solution.

Using MOPS and applicants' dry measurement technique, devices according to the present invention successfully detected the attachment of biochemicals (see FIGS. 9A–9C data). The receptors attached with specific target and were relatively insensitive to non-specific reactions. Applicants' dry measurement technique was also successfully tested with other devices, not herein described. In addition to separating testing and measurement spatially and temporally, dry measurements according to the present invention promote measurement sensitivity contrasted to prior art methods and devices where, in the prior art, ionic shielding or screening greatly limited sensor sensitivity.

If desired after long storage periods, reconstitution of binding conditions may be accomplished by emerging the device in a buffer solution of the same concentration and pH as was used in the original target material binding test. Alternatively, a receptor-prepared unbound device, or a post-binding device may also be stored.

Applicant's dry measurement technique advantageously eliminates the ion shielding problem so prevalent in the prior art. According to the present invention, removing the device 50 from an ionic solution 52 before testing facilitates elimination of the external reference electrode and attendant gate bias problems, drift and potential chemical contamination so prevalent in the prior art. It is understood that at the microscopic level, moisture may still be present on the sensor, and the term "dry" encompasses quasi-dry, to include such microscopic moisture. In the present invention, attached surface charge is sensed directly.

The present invention circumvents the ionic shielding problem that has been so troublesome to the prior art by making post-binding measurements under dry (or at least quasi-dry) conditions. By "quasi-dry" it is meant that possibly at a molecular level some moisture may be present on or about the bound target material 64 (see FIG. 2B). Further, by permitting integration of an attaching target's charge, the present invention permits significantly increased sensitivity over prior art in-solution attempts at transient measurement.

Once a sensor 50 with bound target matter 64 is removed from an ionic test solution 52, the charges associated with the bound matter are no longer shielded by ions in the no longer present solution. As a result, a net charge is manifested at layer 60 generating an associated electric field across the underlying insulator layer 58, 90, 58, 903, 904. This charge and the attendant electric field attract oppositely charged free carrier charges from the semiconductor substrate 56 (or repel like polarity free carrier charges), resulting in opposite charges at or near the surface of the substrate 56.

Contact potential effects at the sensor gate 60 are generally different than the effects of bound charges, and these effects may be distinguished by comparing the influence of target material attachment on the topgate region 90 of two sensor devices 50, 50" identical except for their insulator thickness 91. Effect separation is possible because while the attached charge generates an electric field across an insulator independent of insulator thickness, the contact potential induced electric field is inversely dependent upon insulator thickness. Thus, by making two independent measurements of these two unknowns, attachment charge and potential effects upon sensor device 50 may be separately identified. The present invention advantageously permits incorporation of thick oxide regions that can increase transconductance threshold voltage, corresponding to a transconductance null in gated bipolar and DCBD devices.

Where the desired information is a direct measurement of target material concentration, binding rate of the target material to a receptor, dissociation rate, binding energy, etc., testing may be interrupted before steady state is achieved.

For example, two identical biosensors may be exposed for different times to the test solution, and removed therefrom before steady state receptor saturation attachment occurs. Using known association and dissociation rate data and binding energy data, subsequent measurement can provide confirmational information, for example to exclude false testing where non-specific binding may occur.

Further, test devices with receptors specific to a first target substance known to be in the test solution, for example, human blood plasma, can be included on the same test chip as the test device with receptors for a second target (for example, testing for a specific disease presence). This is especially useful where the first target substance has known aging characteristics, sensitivity to heat, etc, as information is provided on the integrity of the test chip relative to testing for the second target substance of interest.

At a measurement site that may be distant in location and time from the binding site, the device is carefully exposed to a buffered deionized ("DI") water solution whose pH is substantially the same as the test solution pH, and then carefully rinsed with the more of the same solution. According to a preferred embodiment depicted in FIG. 5, substrate 51 can include an on-chip pH sensor 100 and storage mechanism 102 for memorializing the test solution's pH value. The on-chip pH sensor 100 itself may be implemented as a device, according to the present invention, and may include the various enhancement techniques described herein.

Further, various conformational devices, devices for measuring cofactors, and devices for measuring other chemicals of interest, and for measuring chip receptor condition and integrity can be included on the same semiconductor chip. Preferably the sensor system further includes an on-chip mechanism 104 for measuring and storing the pre-attachment quiescent conditions of one or more devices (e.g., 50A, 50B, etc.) fabricated on the same substrate. For ease of illustration, FIG. 5 does not depict the couplings between device 104 and the various sensors.

As depicted by FIG. 5, the sensor system 106 can include measurement circuitry (e.g., 104) for each sensor device, and circuitry providing error alerts where, for example, receptor integrity, storage conditions, etc., are in question. Such on-chip circuitry can include a temperature sensor to monitor incubation conditions present during the chemical reaction of interest (including attachment and dissociation), as well as a clock measuring reaction or dissociation process times. Thus, system 106 can measure physical parameters including reaction temperature, reaction time, solution pH, and ionic concentration.

In the generalized embodiment of FIG. 5, note that it is not necessary that each sensor be identical, either in size, or in the density and/or number of receptor types 66, 66'. For example, sensor 50F includes no receptors and may be coated with an inert material, and may be used as a calibration sensor in that the "before" and "after" binding characteristics of sensor 50F should be the same. Conformational testing excluding a non-specific reaction with device 50F's inert material could be achieved by providing another sensor whose outer film should also be non-reactive with the test solution contents. "Before" binding data from sensor 50F may be stored in device 104 for comparison to the sensor's "after" binding data. If the two sets of data do not agree, a user would know to suspect the integrity of data from sensors 50A–50E.

The present invention also facilitates obtaining sequence information of polymeric molecules such as DNA, RNA, glycoconjugates, polypeptides, and so forth as well, and can detect molecular species subject to electrophoresis or chromatography. For example, the system depicted in FIG. 5 may include a one- or two-dimensional array of sensors arranged in a dense matrix substantially occupying substrate or wafer 51. A matrix of arrays 106 may be used to measure the results of chemical separation processes, such as chromatography, electrophoresis, and the like. As used herein, an electrophoretic gel means any medium suitable for separating particles under an electric field, e.g., polymeric gels such as polyacrylamide, and saccharide gels such as agarose. A chromatographic separation matrix means any medium suitable for chromatographically separating particles, and a centrifugal separation matrix shall include any medium suitable for separating particles subject to centrifugation, e.g., sucrose and cesium chloride gradients. Using these well known techniques, particles may be separated according to charge, structure, binding affinity, size, and the like.

For example, in an electrophoresis application, system 106 may be fabricated adjacent to a matrix 107, e.g., gel, or a gel 107 may be applied to the upper surface of system 106. (In a chromatographic application, a thin-layer calcium carbonate 107 could be used instead.) In the course of electrophoresis, charge-bearing molecules are caused to drift or migrate, forming electrophoretic target bands shown generally as 109. The position and characteristics of these bands can provide useful information. The location and magnitude of band-associated charges may be sensed by the underlying matrix of sensors and detected with sensitivity greater than what is provided by conventional optical electrophoresis measuring devices. Preferably an on-chip signal processor 111 processes the sensor outputs to provide a video representation of the magnitude and location of these charges, for example on a monitor 113. The present invention thus permits charge sensing (during or after separation), and electronic display and signal processing of electrophoresis data in real time.

The embodiment of FIG. 5 also promotes confirmatory testing not merely of the devices themselves, but of various target materials. For example, device 50B has a greater density of the same type of receptors than does device 50A. Therefore confirmation of binding the appropriate target material for receptors 66 would be indicated by a proportionally greater binding effect upon device 50B contrasted with device 50A.

Further, by providing some devices with only a first type of receptor (e.g., device 50A), and some devices with only a second type of receptor (e.g., device 50C), a differential analysis of a binding event may be made. For example, a target substance suitable for binding only with receptors 66 should produce a measurable change in device 50A, but not in device 50C. Further, a device such as device 50E may include both sensor types to provide still further confirmatory information as to the nature of what the binding substance is. Additional confirmational data may be acquired by re-exposure of a previously exposed test device to a different temperature, different pH, different chemicals, etc., providing known results for the target material. For example, disassociation rate of nucleic acid components with temperature, dissociation with pH change, charge change with pH change, charge sign change with pH change, disassociation as a function of different receptor binding sites, etc., provide useful information, especially as to whether what bound to the receptor of interest was in fact the desired target material.

The ionic attachment signals can be increased in various ways by increasing the number of ions attached to a specific chemical species used for a receptor. This receptor may be the first receptor biochemical layer or may be the top layer in a molecular sandwich. The chemical reactive molecule is tagged with some appropriate means so its presence can be detected, for example.

Differential analysis could also be performed by exposing two identical sensors to a target material for different time lengths, each shorter than the time known to be required for the target-receptor reaction to complete. Charge measurement for each device provides data for target material reaction (or attachment) rate, and concentration in the test solution, data useful to provide species identification. Those skilled in the relevant art will appreciate that information useful for biochemical characterization including confirmational testing may be acquired using environmental variations and timed measurements. For example, attachment rates, solution target concentration, receptor-bound target concentration, attachment and dissociation kinetics and related activation energies may be determined using multiple measurements made at different times, with varying temperature, test solution pH, and other environmental parameters.

Whether measurements are conducted wet (as depicted in FIG. 3A) or dry/quasi-dry (as depicted in FIG. 3B), the bound charges result in an electric field that can modulate the conductance of the device semiconductor channel (if not neutralized by shielding, etc.). This modulation permits detection using suitable equipment 70, according to the present invention. While the description thus far has been with respect to a sensor 50 such as depicted in FIGS. 3A and 3B, according to the present invention, other semiconductor field effect sensors including the embodiment of FIG. 4 (and devices functionally similar thereto) could also be used.

In applicant's dry measurement process, preferably receptor layer 60's outer surface repels free ions in the ionic test solution that could otherwise result in undesirable shielding. This is analogous to a solid/liquid phase segregation phenomenon, wherein dry biochemical layers (e.g., receptors 66, layer 90' in FIG. 2B) do not readily retain extra free solution ions. Stated differently, it is desired to create a condition whereby free ions prefer to remain in the test solution (where they can no longer shield charges attached to device 50), rather than remain with the device as and after it is removed from the test solution.

It is sufficient for the present invention that after removal from the test solution and drying, there remain a net charge associated with the bound target material, which charge can be used to identify and preferably quantify the target material. Generally, applicant's method of dry measurement substantially preserves chemical specificity as to the bound target material. The invention does not necessarily require that the receptor or receptor-bound target material preserve the charge configuration attained in the test solution. For example, reinsertion of the sensor into an appropriate measuring solution can provide an appropriate chemical environment for following specific reactions. Specific reaction features as preservation after drying and reconstituting a receptor surface are known to those skilled in radioimmunassays which require the storage of glass or polymer beads with receptors attached.

Understandably, because dry testing according to the present invention overcomes ionic shielding problems, sensors such as depicted in FIGS. 2B and 3 are very sensitive. Further, because of the inherent sensitivity now available, devices according to the present invention especially benefit from sensitivity enhancement techniques that permit meaningful quantitative and qualitative measurements on a scale not available in the prior FET sensor related art.

It will be appreciated that charge sensitivity will vary with the density of binding sites or charges attached thereto. Because applicants' devices can exhibit increased and enhanced sensitivity, smaller devices (using less potentially expensive or scarce receptor material 66) may be used. Many different types of receptors 66, 66' may be used on a single sensor (see FIGS. 2A, 2B) to permit simultaneous testing for multiple targets, including screening and differential analysis testing.

It is important to appreciate that a device according to the present invention need not employ a conducting channel. FIG. 6A, for example, depicts a biosensor field effect capacitor device 50" that has no channel per se, but still senses chemical associated charge, by sensing capacitance related changes due to surface potential. Device 50", for example, includes a semiconductor substrate 56" (here shown as p-type, although n-type could be used instead) whereon an n-region 57' is deposited, forming a PN junction, an insulating layer 58 (e.g., $SiO_2$), and a topgate 90 including receptors 66 to which charged targets 64 can attach. Upon attachment, the voltage across the capacitor consisting of the charged surface 90 and the opposing "plate" underlying substrate p-region changes, thereby changing the surface potential at the insulator-semiconductor interface 71. This attachment-induced potential change alters the surface recombination velocity (i.e., surface lifetime) at the interface 71 under the target region. Surface excess carrier recombination is a strong function of the interface 71 surface potential, and the forward bias diode current characteristic can be changed by the target induced surface potential change. When the PN diode is forward biased, electron-hole pairs are injected into the substrate, some of which diffuse and recombine at surface 90 with a lifetime dependent upon target-charge induced surface potentials. Because of the strong surface recombination-surface potential relationship, the pre-attachment value of surface potential directly influences detection sensitivity via inspection of diode current. The surface potential can be set to an optimum value using a buried gate 61 and appropriate bias for a preselected recombination sensitivity to target charge attachment 64 at topgate region 90. In this fashion, even though no channel is present, device 50' senses attached charge. Because such bipolar PN devices as 50' exhibit a gate-influenced behavior, they may properly be termed gated bipolar devices.

FIG. 6B depicts an alternate embodiment of a device 50' comprising a semiconductor substrate 56, an insulating layer 58 (e.g., $SiO_2$ with an appropriate moisture blocking layer) that surrounds a buried gate 61, and a topgate 90 that includes receptors 66 that can attach to targets 64. Buried gate devices may be realized using the same technology used in fabrication of digital ROM/RAM memories. This structure forms an equivalent capacitor $C_{eq}$ having plates formed by gate 61 (whose charge reflects charge at surface 90) and charge-influenced field effect region 63 in the underlying substrate 56. An external capacitor 82 couples an external signal to buried gate 61, establishing a pre-attaching bias condition for device 50'. A buried gate structure advantageously permits creation of a predetermined operation condition. See also, by way of further example, the DCBD device of FIG. 4. Establishing a suitable pre-attachment bias condition permits selecting a desired device sensitivity range and allows, if desired, establishing a threshold trip point causing the device to substantially change state upon the target attachment. For example, pre-biasing a DCBD can produce in a designed signal shift in transconductance (and in switching of an attached second device), or substantial decrease in transconductance or current gain ($\beta$), to achieve maximum sensitivity.

As noted elsewhere herein, applying bias directly to gate 61 is not desired because charge attaching to surface 90 will in essence be "shorted out" and not induce a charge effect on the adjacent field effect region 63. However capacitor 82 permits establishing a desired pre-attachment bias state, without shielding region 63 from attached charge at surface 90.

The sensor device of FIG. 6B can be used as a simple capacitor component in an RC oscillator, where the device interface 71 is biased to flat band or just into depletion. Target induced charge will change the depletion width and thus the depletion capacitance. Since charge Q across a capacitor C is proportional to the product of the capacitor C and voltage across the capacitor, charge at surface 90 depletes the underlying region, thus modulating capacitor $C_{eq}$. An external circuit 67 (e.g., an RC-dependent oscillator) may be coupled to gate 61, such that attachment charge alters the frequency of circuit 67, which frequency may be read by a counter 69. The target-induced change in gate capacitance, and thus the shift in frequency of oscillator 67, preferably is maximized. Maximization results by selecting insulator 65 to be as thin as possible, and the underlying substrate region to be very lightly doped, whereby target-induced depletion width change and related gate capacitance change are maximized.

While FIGS. 2 and 4 depict biosensors according to the present invention that are fabricated vertically on a typically silicon substrate wafer, other configurations are also possible including, by way of example, lateral architectural devices, and channel devices buried in an insulating substrate such as depicted in FIGS. 6C and 6D. The conducting channels in such devices may advantageously be fabricated of polysilicon. Devices such as those shown in FIG. 6D do not require a semiconductor substrate (although one can be used) and such sensor devices may be fabricated in arrays on a low cost insulator substrate, for electrophoresis pattern measurements, for example.

FIG. 6C depicts a device 50 having a preferably polysilicon gate 901 buried in a layer of insulating material 903, 904 (e.g., $SiO_2$ coated with a suitable moisture blocking insulator) underlying a surface 90 containing receptors 66. Depletion on the lower depletion region 912 of the polysilicon resistive gate 901 can occur and be varied by application of a backgate bias $V_{bg}$ to backgate 62 from potential source 905 preferably via capacitor 906. Depending upon charge attachment to receptors 66, upper depletion region 914 of the channel 901 may be caused to deplete, accumulate or be inverted. Backgate bias sensitivity may be enhanced by making the underlying insulator region 904 thicker, since so doing will require a larger magnitude of $V_{bg}$ to restore the conductance of channel 911, e.g., the polysilicon gate, to a preattachment state. Shown in phantom in FIG. 6C are intrinsic capacitance $C_{BIO}$ between layer 90 and upper region 914, and intrinsic capacitance $C_{BG}$ between lower region 912 and the backgate substrate 920.

FIG. 6D shows yet another embodiment, wherein device 50 includes a second conducting gate 921, separated by insulator material 904 from channel region 911, as above-described. In this embodiment, restorative backgate bias is preferably capacitively coupled to this second gate 921, which bias is coupled via the intrinsic insulator capacitance $C_{BG}$ to restore conductance of channel 911 to a preattachment state. Again, a signal characterizing the attachment to receptors 66 may be obtained by monitoring the restoration bias signal $V_{bg}$. The capacitor 906 may be eliminated (e.g., shorted out), such that conducting gate 921 is directly coupled to the backbias source 905.

FIG. 6E shows an embodiment of a device 50 wherein part of the insulator-surrounded 901, 902 polysilicon channel, or resistor, 911 is doped 902 to form a lateral PN junction 930, within an polysilicon region 901 (here, n-type). This structure presents a channel resistance 931 that may be modulated from above by targets attaching to receptors 66 on layer 90, and from below by a first backgate bias $V_{BG}$ from potential source 905. A second backgate bias 906 is dropped across the p (902) n (911) junction to modulate the channel resistance 931, which is to say across the laterally PN junction depletion region 930. (In FIG. 6E, it is understood that $I_{ds}$ flows into the diagram.)

Alternatively, devices with vertical channels may be used with a biochemically receptive gate region located laterally in a mesa-etched channel, or as shown in FIG. 6D, with multiple buried polysilicon resistor sensor regions 940.

FIG. 6F depicts a device 50 that includes a topgate 600 that may be, but preferably is not, exposed to the test solution (e.g., solution 52) and is preferably protected by an insulator layer 553 such as parylene. Buried gate 600 may be fabricated from polysilicon, among other materials. Buried gate 600 may be used in combination with a receptor bearing topgate 60 using a suitable insulator to insulate gate 600 from test solution contact, and/or used in combination with a preferably AC-coupled source of backgate bias 74, 234.

As noted, conducting gate field effect devices can be difficult with respect to biasing. If the conducting gate is DC coupled directly to an ideal power supply 520 (e.g., without blocking capacitor $C_B$ 502), charge will flow between the buried conducting gate 600 and the power supply 520. As a result, a biochemical target charge induced on gate 600 will be exchanged with the power supply 520, effectively removing the field effect region from influence by the biochemical charges. However, this problem can eliminated by series coupling a blocking capacitor $C_B$ 502, as shown in FIG. 6F. Capacitor 502 permits an effective DC bias or a pulsed or AC bias to be applied to the biasing gate 600, with respect to the adjacent field effect region 542.

Incorporating a buried gate 600 can provide many useful functions for chemical sensing. For example, as shown in FIG. 6F, a power source 520 suitably coupled to the buried gate 600 can establish a desired bias with respect to the potential at a device node 541 (e.g., backgate substrate). As a result, the underlying field effect region 542 can be biased to a predetermined desired operating characteristic, such as a condition maximizing biochemical detection sensitivity. The backgate bias 74, 254 may be varied to restore a preattachment operating condition and the restoring potential measured. Alternatively, the field effect region can be restored to a predetermined operating characteristic after attachment using DC, AC or pulsed gate 600 bias 520, or the device condition may be measured without restoring the preattachment operating condition.

Where AC or pulsed source 520 couples bias to gate 600, the bias signal may be coupled via lead 530 to an amplifier 528 for sensitivity enhancement purposes. Alternatively, the bias voltage present at the conducting gate 600 itself may be coupled (shown as phantom line 506) to an amplifier for increased sensitivity.

The magnitude of blocking bias capacitor $C_B$ 502 may advantageously be used to affect a desired voltage division between capacitances $C_b$ and $C_g$, or to alter the relative fraction of the attachment charge influencing the underlying field effect region 542. For example, when sensing target-induced frequency shift in an oscillator 67 for a desired sensed parameter change, capacitor $C_b$ is selected such that essentially all of the target charge is induced on $C_g$, and then on the underlying substrate. Doing so maximizes charge influence on the underlying field effect region 542. And, assuming that gate 600's bias supply 520 is adjusted to provide a flatband condition at the semiconductor insulator surface. Charge attaching to receptors 66 will induce a depletion region at the surface, whereupon the gate-substrate capacitance $C_g$ is altered. Measurement of this charge may be sensed by incorporating of $C_g$ into an RC oscillator, whose frequency perturbation reflects charge-induced capacitance change, thus providing enhanced detection sensitivity.

Further, suitably biasing buried gate 600 advantageously can expose the region adjoining gate 600 to an electric field or voltage. One exemplary application is the use such biased buried gates to maintain desired electric field drift orientation in electrophoresis charge sensing arrays. Alternatively, the applied buried gate bias can be adjusted to attract electrophoresis particles to the top insulator region 91, in closer proximity to the underlying field effect region 542. Further, by using multiple gates two adjacent buried gates may be biased so that electrophoresis components having differing charge sign (e.g., arising from application of a particular solution pH) can be separated. Separation would result in a first target being attracted to a first buried gate, and a second target of opposite polarity being attracted to a second buried gate or to the immediately adjacent insulator material.

Additional advantages of buried gate devices include the opportunity to make insulator 59, 554 relatively thick, such that the resultant threshold voltage shift (or transconductance threshold voltage shift in a DCBD) is relatively large. Because null measurement of DCBD transconductance threshold voltage shift can be accurately made, substantially enhanced sensitivity is provided for measuring target attachment.

Figure 6G:
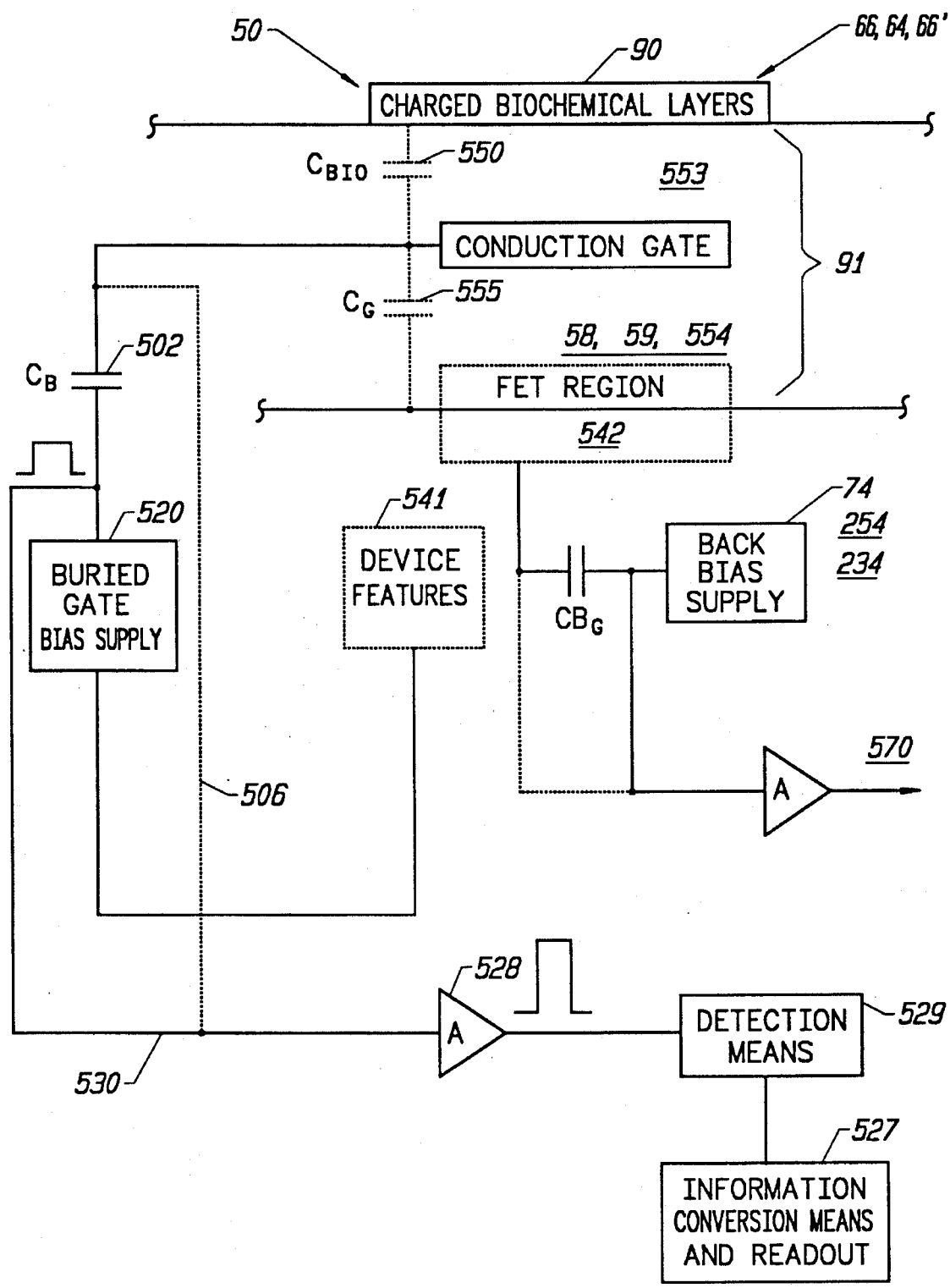
FIG. 6G depicts a buried gate embodiment with capacitively coupled biasing and nodes coupled to various signal enhancement circuitry.

FIG. 6G depicts a buried gate semiconductor device 50 as including a first insulator region 59, 554 located between a field effect device region 542 and a buried gate 600, a second insulator region 553 located between the buried gate 600 and the topgate region 90. Collectively, the full insulator region is denoted 91. FIG. 6G further depicts a backgate bias blocking and voltage dividing capacitor $C_B$, and information conversion circuitry 527, with further, optional, sensitivity enhancing circuitry and/or devices indicated generally by arrow 570. In FIG. 6G, device 50 is depicted generically and is understood to potentially include any of the devices described herein, and therefore source, drain, backgate, etc. regions, if present, are not depicted. For the same reason, conducting masking, blocking layers, and the like (all described elsewhere herein) are not depicted, but are understood to be present as appropriate. Because buried gate devices may be realized using the same technology used in fabrication of digital ROM/RAM memories, fabrication details are not presented here.

Figure 7B:
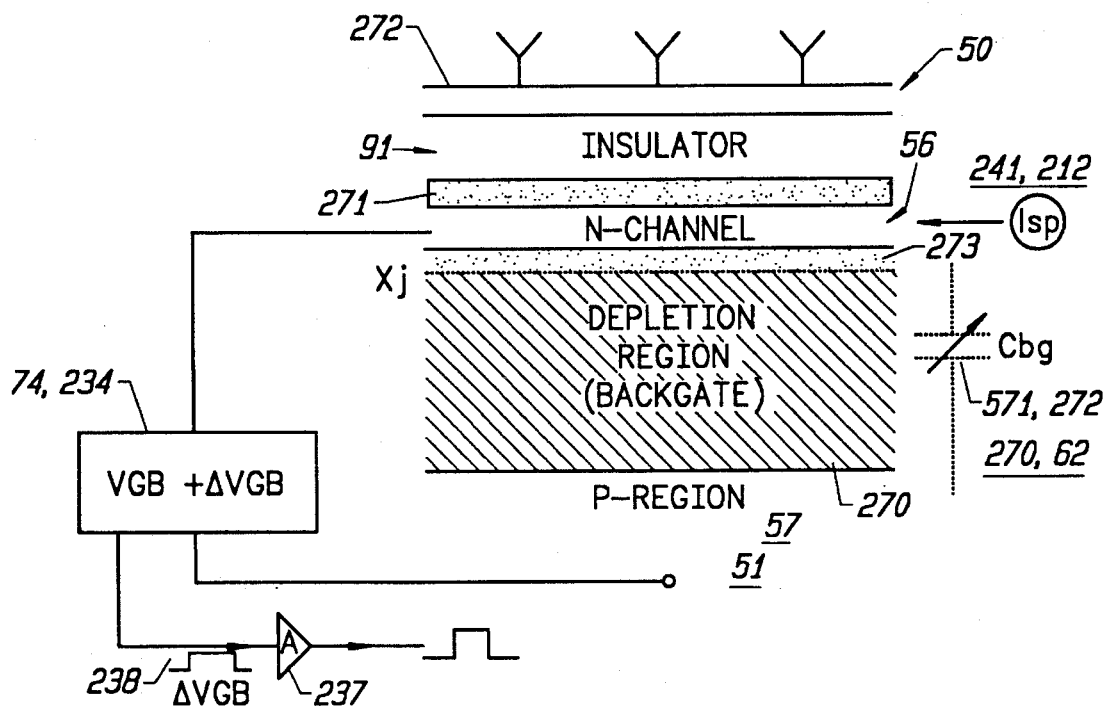
FIG. 7B depicts an embodiment wherein device current is constant and back bias is modulated and sensed.

Turning now to FIGS. 7A and 7B, two embodiments of feedback for sensor reset and sensitivity enhancement measurement approaches are shown. In FIG. 7A, sensor 50 is biased by a pulsed backgate bias supply 234, to reset or restore device 50 to its preattachment condition, while measurement system 230 monitors a device operating parameter sensitive to charged target attachment. For ease of illustration, parameter measurement system 230 is indicated generally, without a specific coupling 232 to the device to illustrate that the chosen parameter(s) may be varied, and can include current, voltage, transconductance, etc. The sensed parameter provides a feedback signal to feedback system 240 that, in response, adjusts the backgate operating voltage to restore the preattachment conditions.

In FIG. 7A, the reset voltage from supply 234 is coupled to the input gate 216 of a second device 217, FET 2, selected for high gain (e.g., a thin gate oxide device). In this cascode circuit, the output reset signal from backgate power supply 234 is coupled to the gate of a second FET device 200. The output current $I_d$ 212 from device 200 is used to detect the target attachment event. Further, this output signal 212 may be processed with circuit 215 to provide additional information, and/or may be coupled to a feedback circuit 240 (shown in phantom) for restoring (or partially restoring) preattachment device 50 conditions. If desired, FET 2 may be a component in a circuit whose performance is affected by FET 2's change in channel resistance responding to attached charge at device 50. For example, if FET 2 affects the frequency of an oscillator 210, attachment at device 50 may be sensed by monitoring frequency change at oscillator 210.

In FIG. 7B, a constant current is maintained in device 50, whereupon a certain voltage is seen across device backgate 270. Charge attaching to the topgate 272 of device 50 will induce a backgate voltage change, which change provides a measure of the attached charge. The current $I_d$ may be AC pulsed, which allows AC amplification 237 without problems associated with DC amplifier drift.

According to one aspect of the present invention, a blocking agent is sequentially applied to the sensor before attempting to measure the desired target material. For example, if receptors 66 are dedicated for attachment to a human antibody, a suitable blocking agent 210 might be bovine serum albumin (BSA). Attachment of a suitable blocking agent 110 may produce a change in charge seen by device 50 (as shown in FIG. 9B, graph e).

Device 50 is then carefully rinsed, preferably in a solution having the same pH as the desired test solution, and in a second sequence, sensor 50 is exposed to a test solution containing target material 64. Since the effect of any charge from the first sequence may be determined (see for example FIGS. 9A–9C) and biased out or otherwise accounted for, the net charge due to target material 64 attachment may be determined, either in wet or dry measurement.

Figure 8A:
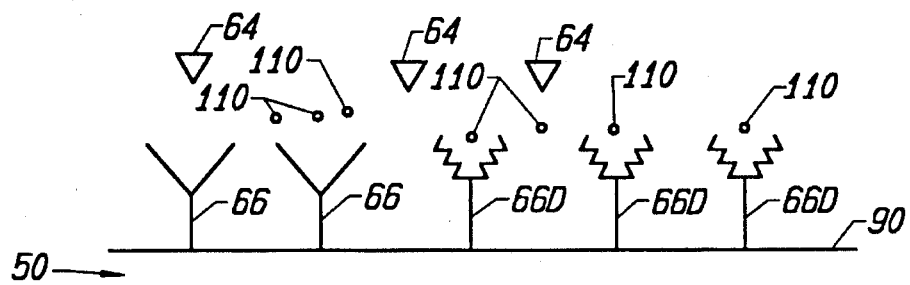
FIG. 8A depicts sequential use of a blocking agent, according to the present invention.
Figure 8B:
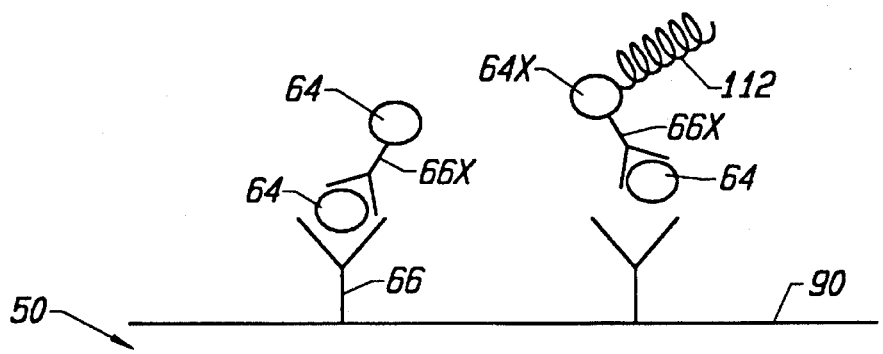
FIG. 8B depicts the use of sandwich-like structures and conglomerates to enhance detection, according to the present invention.

Because the present invention senses charge change associated with a desired binding event, applicant's devices exhibit more sensitivity when the bound target is associated with a relatively large charge. In another aspect, the present invention provides passive enhancement of binding charge associated with a desired attachment using a "sandwich" technique. As depicted in FIG. 8B, in a first sequence, a target 64 having a certain charge binds in a test solution to a receptor 66, producing electrical change (e.g., channel conductance change) in the underlying device 50. Device 50 is then rinsed, preferably in a solution whose pH is that of the original test solution, and exposed to a solution containing a blocking agent, and retested. Device 50 is then exposed to a solution (whose pH preferably is that of the original test solution) containing receptors 66X that will bind to the remaining fraction of the previously bound targets 64. In a third sequence, the device 50 may be exposed to a similar pH test solution (after blocking agent treatment and measurement) containing target material 66, that will bind to the new collection of bound receptors 66X. The blocking agent process may be used after every target and receptor attachment process to suppress or eliminate non-specific binding sites.

In this example, the net charge upon device 50 from target 64 has been increased, including charge effects from the additional attachment of receptors to the "sandwich". Other means of enhancing or amplifying the signal generated by target binding are also possible. For example, as depicted in the right-hand portion of FIG. 8B, a conglomerate may be used in the third sequence, wherein device 50 could be exposed to material having substantially more charge than target 64. For example, such material might include a DNA sequence 112 attached to a target substance 64X that will bind to the receptor 66X. In this fashion, a substantially larger net charge attaches to the device, resulting in a larger signal. It is understood that charge associated with receptor 66 and target 64 may be additive or subtractive, as may also be the case with material 66X, 64X and 112.

Figure 8C:
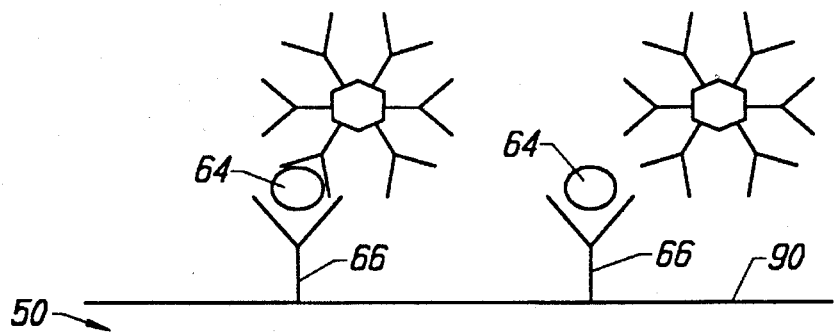
FIG. 8C depicts the use of beads to enhance detection, according to the present invention.
Figure 8D:
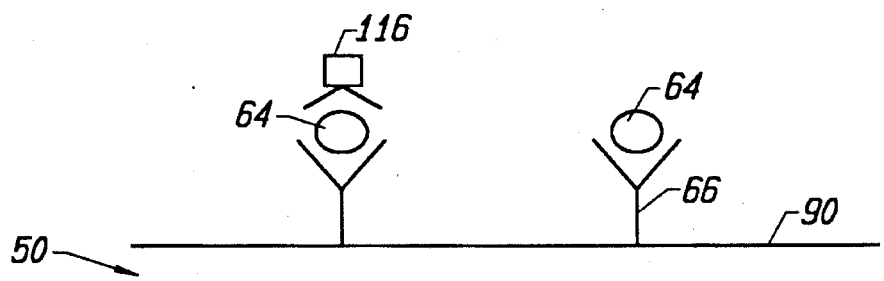
FIG. 8D depicts the use of conjugates to enhance detection, according to the present invention.

FIG. 8C depicts the use of beads as an alternative (or additional) method of passively enhancing device sensitivity. Beads 114 may have a variety of shapes, are commercially available in sizes ranging from less than 0.1μ to several μ, and are typically made of glass or a polymer, or Si, or magnetic material, etc. Receptors 66' have similar selective reactivity characteristics as the primary receptors 66, and may in fact be identical thereto. Alternatively, the charge enhancing receptors 61' may be different from primary receptors 66 and, for example, may be specific to a particular DNA fragment carrying very large quantities of charge. Conjugates are frequently made from gold, biotin, ferritin, and the like, and may be made from other chemicals such as nucleic acid chains and antibody chains. In a second sequence, after target 64 has bound to primary receptor 66, the device 50 is exposed to a solution containing conjugated receptors 116.

With reference to FIGS. 9A–9C, the drain current (Ids) and drain-source voltage (Vds) for sensor 50 was dry measured, according to the present invention, after the application of various biolayers. The device under test was removed from the target solution, rinsed with a buffer of substantially the same pH as the test solution, and gently dry blown using dry nitrogen. For the data shown in these figures, incubation was 27° C. with a 10 mM MOPS buffer employed to maintain pH≈7. With reference to FIG. 9B, for example, the device was tested before and after application of a parylene film 90 (bar graphs a and b). After stabilizing the device in a MOPS buffer solution measurements were again taken (bar graph c). A receptor layer (receptor:IgG) was applied, and measurements taken (bar graph d), after which the device was exposed to a BSA blocking agent and measured (bar graph e). The utility of the BSA blocking layer is shown by bar graph f (FIG. 9B), wherein the device was exposed to a non-specific antibody. As shown by bar graphs e and f, there was relatively little change in charge from non-specific bindings, which indicates BSA suppression of non-specific binding. Next the device was exposed to a desired target substance (antigen: Goat anti-IgG), and a change in charge (ΔQ) was noted (bar graph g). Finally, the device was reexposed to receptor material (IgG), which resulted in essentially the same charge change (ΔQ). It is noted from FIGS. 9B and 9C that different chemical exposure and reactions can result in charge attachment of different polarities, as indicated by the direction of the bar shift after exposure to subsequent chemical exposure.

The present invention advantageously may be reused by suitably denaturing sensor 50, preferably by boiling in water for perhaps five minutes, or by use of chemicals, e.g., sulfuric acid. Denaturing appears to remove the chemical specificity of original primary receptors 66, and any attached subsequent chemical species, and further conditions sensor surface 90 and/or these receptors to become chemical active. This in turns permits acceptance of a second generation of receptors that may differ from the first generation in specificity.

Bar graph a in FIG. 9C depicts a denatured device 50. After denaturing, the device was exposed to a buffered MOPS solution (bar graph b), which altered the effective charge on the device. Thereafter in a suitable incubation environment, receptors were attached (bar graph c), which in this case altered the gate attached charge. Exposure to a BSA environment (bar graph d) slightly changed the charge, and exposure to the target material (bar graph f) resulted in a desired perceptible charge change $\Delta Q$.

Automated testing is readily implemented using the invention, which can include on-chip testing circuitry (see FIG. 5). Dry testing particularly promotes automated procedures, where the bound sensors may be automatically delivered to a test fixture (e.g., a test probe), where test information is read and the test results stored for automatic computer processing.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A biosensor field effect capacitor device for sensing the presence of a target in a first solution, the device comprising:

a substrate;

an upper region producing a first electrical signal in response to said target's presence, said upper region overlying said substrate;

an insulating layer, separating said upper region and said substrate;

a depletion field effect region in said substrate having a depletion width characteristic influenced by said first electrical signal; and means for detecting changing surface potential at an interface between said insulating layer and said substrate, said means comprising a diode junction, spaced-apart from said upper region and in field effect communication with said depletion field effect region and means for measuring changing diode junction current in response to said target presence;

wherein said target's presence modulates said depletion region producing a change in at least one of depletion width capacitance and surface recombination velocity.

2. The device of claim 1, further including resonant means, coupled to said device, for varying a detectable resonant frequency in response to presence of said target.

3. The device of claim 1, wherein said field effect region includes a semiconductor conducting channel.

4. The device of claim 3, wherein said substrate is selected from the group consisting of (a) a semiconductor substrate, (b) an insulating substrate, and (c) a conducting substrate.

5. The device of claim 1, wherein said target is a particle.

6. The device of claim 1, wherein said gate is a gate selected from the group consisting of (i) a buried gate, (ii) a conducting gate, (iii) a gate is disposed beneath said depletion field effect region, and (iv) a gate formed adjacent said depletion field region.

7. The device of claim 1, further including means, coupled to said diode junction, for enhancing an output signal indicating presence of a said target.

8. The device of claim 1, further including means, coupled to said diode junction, for reestablishing a pre-target-presence characteristic of said device.

9. The device of claim 8, wherein said conducting gate couples to a power supply through a blocking capacitor.

10. The device of claim 1, wherein said upper region has a characteristic selected from the group consisting of (i) said upper region is a topgate, (ii) said upper region floats electrically, and (iii) said upper region includes a chemically selective material.

11. The device of claim 1, wherein said upper region floats electrically, and wherein said first electrical signal is produced upon attachment of said target.

12. A semiconductor device for sensing the presence of a target in a solution the device comprising:

a substrate;

a topgate region producing a first electrical signal in response to said target's presence, said topgate region overlying said substrate;

a second gate region, coupling a second electrical signal to and from said device;

a field effect region disposed in said substrate such that conductance of said device is modulated by an electrical signal from at least one of said topgate region and said second gate region;

wherein said first electrical signal modulates conductance of said device and said device provides an output signal indicating attachment; and means, coupled to said second gate region, for enhancing said output signal indicating attachment of a said target.

13. The device of claim 12, wherein said field effect region has a characteristic of at least a chosen one of the group consisting of a junction field Field Effect Transistor channel, a Metal Oxide Silicon Field Effect Transistor, and channel, a Metal Insulator Semiconductor Field Effect Transistor channel, an Ion Selective Field Effect Transistor channel, an inversion Field Effect Transistor channel, an accumulation FET channel, a Metal Semiconductor Field Effect Transitior channel, a HETEROJUNCTION Field Effect Transistor channel, a depletion mode Metal Oxide Silicon Field Effect Transistor, a Distributed Channel Bipolar Device, a transistor, and a capacitor.

14. The device of claim 12, wherein said means includes means for monitoring a parameter of said device, and bias means for adjusting a bias at said second gate after attachment to at least partially restore said parameter to a preattachment state, wherein the magnitude of bias adjustment provides a measure of attachment.

15. The device of claim 12, wherein said second gate comprises a semiconductor junction doped to cause a small fraction of an applied second gate bias voltage to modulate said channel conductance.

16. The device of claim 12, further including a conducting gate, said conducting gate is coupled to a power supply through a blocking capacitor.

17. The device of claim 16, further including an insulator, disposed between said topgate region and said field effect region.

18. The device of claim 12, further including attachment means, coupled to said topgate region, for enhancing an output signal indicating attachment of a said target.

19. The device of claim 12, wherein said means includes means for monitoring a parameter of said device, and bias means for adjusting a bias at said topgate region after attachment to at least partially restore said parameter to a preattachment state, wherein the magnitude of bias adjustment provides a measure of attachment.

20. The device of claim 12, further including:
electrical means, on said substrate, for measuring at least one parameter of said solution.

21. The device of claim 20, further including a storage means, on said substrate, coupled to an output of said first electrical means for memorializing at least one parameter of said first environment.

22. The device of claim 20, wherein said first environment includes at least one member selected from the group consisting of a solution, and an electrophoresis separation gel.

23. The device of claim 20, wherein said device is a sensor that includes chemically selective material region.

24. The device of claim 23, wherein said chemically selective material region is produced by patterning.

25. The device of claim 20, further including a layer of material selected from the group consisting of (a) shield material disposed as to selectively shield a region proximate to said field effect region, (b) a layer of inert material disposed to selectively protect a region proximate said field effect region, and (c) a patterned layer of material disposed to selectively influence a region underlying said material in response to said target presence while immersed in said solution and after removal from said solution.

26. The device of claim 12, wherein said first environment is a solution.

27. The device of claim 12, wherein said top region floats electrically.

28. The device of claim 12, wherein said second gate is selected from the group consisting of (i) a buried gate, (ii) a conducting gate, (iii) a gate that is a PN junction, (iv) a gate that is a semiconductor-insulator interface gate, (v) a gate disposed beneath said field effect region, (vi) a gate disposed adjacent said field effect region, and (vii) a P-I-N gate.

29. The device of claim 12, further including a third gate, spaced-apart from said topgate region and in field communication with said field effect region.

30. The device of claim 29, wherein said third gate is selected from the group consisting of (i) a buried gate, (ii) a conducting gate, (iii) a gate that is a PN junction, (iv) a gate that is a semiconductor-insulator interface gate, (v) a gate disposed beneath said field effect region, (vi) a gate disposed adjacent said field effect region, and (vii) a P-I-N gate.

31. The device of claim 12, wherein said means for enhancing includes means for monitoring a parameter of said device, and bias means for adjusting a bias at said second gate to modify measurement sensitivity of said device to attachment by a said target.

32. The device of claim 12, wherein said means for enhancing includes a second semiconductor device having an input lead coupled to said semiconductor device.

33. A method for detecting the presence of a target particle in a solution by use of a field effect device that includes a surface to which a target particle bindingly attaches, the method comprising the following steps:
exposing said device to said solution said attachment leading to an alteration of at least one parameter of said device from a preattachment state;
removing said device from said solution;
measuring, in an environment, said at least one parameter to determine whether attachment of said target particle occurred;
wherein said environment is selected from the group consisting of (a) a gas, (b) a liquid, and (c) a solution.

34. The method of claim 33, wherein said solution is an aqueous solution.

35. The method of claim 33, wherein said solution is an in-vitro solution within a living animal.

36. The method of claim 33, wherein said environment differs from said solution in at least one characteristic selected from the group consisting of (a) a difference in ion concentration, (b) a difference in temperature, and (c) a difference in chemical composition.

37. The method of claim 33, further including the step of providing means for modifying charge associated with said attached target.

38. The method of claim 37, wherein said means are provided in said environment.

39. The method of claim 37, wherein said step of providing means for modifying charge includes the use of at least one mechanism selected from the group consisting of (a) beads, (b) conjugates, (c) conglomerates, and (d) sandwich-like structures.

40. The method of claim 33, wherein said device includes a surface having a chosen region receptive to said attachment, said chosen region resulting from a step selected from the group consisting of (a) embedding a shielding layer in said device during device fabrication, which layer shields said device save for a region underlying said chosen region, (b) forming a pattern mask of inert material on all of said surface save for said chosen region thereof, (c) forming a pattern mask of material on said surface save for said chosen region thereon, said material is selected to influence a region underlying said material in a set manner, and is in response to at least one of said solution and said environment.

41. The method of claim 33, wherein between said step of exposing and said step of measuring, a time interval passes, which time interval has a duration selected from the group consisting of (a) at least an hour, (b) at least a day, and (c) at least a week.

42. The method of claim 33, further including the step of enhancing sensitivity of said step of measuring.

43. The method of claim 42, wherein said step of enhancing including a step selected from the group consisting of (i) varying a bias coupled to said device to restore a preattachment value of said at least one parameter, and then measuring bias magnitude required to so restore, (ii) prebiasing said device to a regime associated with high device attachment sensitivity, and (iii) coupling a second device to said device such that said at least one parameter modifies a parameter of said second device, which second device parameter is then measured.

44. The method of claim 33, wherein said device is a field effect device, and wherein said at least one parameter is selected from the group consisting of (a) drain-source current, (b) threshold voltage, (c) gate-source voltage, (d) pinchoff voltage, (e) transconductance, (f) conductance, (g) gate-source capacitance, (h) gate-substrate capacitance, (i) drain-source current, (j) change in drain-source voltage for constant drain-source current, (k) transconductance threshold voltage, and (l) contact potential.

45. A method for detecting the presence of a target particle in a matrix comprising particles separated from a mixture, the method comprising the following steps:
exposing to said matrix a plurality of charge sensing devices disposed on a substrate, wherein each said device includes a surface and at least one device parameter that is altered when said surface comes in charge communication with said target particle; and
measuring said at least one parameter to determine when said surface came in charge communication with said target particle.

46. The method of claim 45, wherein said plurality of charge sensing devices are disposed as an array permitting positional detection of said target particle on said matrix.

47. The method of claim 45, wherein said matrix is selected from the group consisting of (a) an electrophoretic gel, (b) a centrifugal separation matrix, and (c) a chromatographic separation matrix.

48. The method of claim 45, wherein said charge sensing devices include at least one field effect device.

49. The method of claim 48, wherein said at least one parameter is selected from the group consisting of (a) drain-source current, (b) threshold voltage, (c) gate-source voltage, (d) pinchoff voltage, (e) transconductance, (f) conductance, (g) gate-source capacitance, (h) gate-substrate capacitance, (i) drain-source current, (j) change in drain-source voltage for constant drain-source current, (k) transconductance threshold voltage, and (l) contact potential.

50. The method of claim 45, including the further step of enhancing said step of measuring, wherein said step of enhancing includes a step selected from the group consisting of (i) varying a bias coupled to said device to restore a pre-attachment value of said at least one parameter, and then measuring bias magnitude required to so restore, (ii) pre-biasing said device to a regime associated with high device attachment sensitivity, and (iii) coupling a second device to said device such that said at least one parameter modifies a parameter of said second device, which second device parameter is then measured.

* * * * *